United States Patent
Seth et al.

(10) Patent No.: US 12,419,800 B2
(45) Date of Patent: Sep. 23, 2025

(54) ORTHOPEDIC SYSTEM AND METHOD OF CONTROLLING THE SAME

(71) Applicant: VISPALEXO INC., Indianapolis, IN (US)

(72) Inventors: Ajay Seth, North Canton, OH (US); Jeffrey A. Denune, Indianapolis, IN (US); Chandan K. Sen, Indianapolis, IN (US); Tyler Crockett, Massillon, OH (US); Kristal Barrick, Massillon, OH (US); Tiffany Wonsick, Massillon, OH (US)

(73) Assignee: VISPALEXO INC., Indianapolis, IN (US)

( * ) Notice: Subject to any disclaimer, the term of this patent is extended or adjusted under 35 U.S.C. 154(b) by 938 days.

(21) Appl. No.: 17/434,575

(22) PCT Filed: May 21, 2021

(86) PCT No.: PCT/US2021/033629
§ 371 (c)(1),
(2) Date: Aug. 27, 2021

(87) PCT Pub. No.: WO2022/076039
PCT Pub. Date: Apr. 14, 2022

(65) Prior Publication Data
US 2023/0065877 A1    Mar. 2, 2023

Related U.S. Application Data

(60) Provisional application No. 63/089,883, filed on Oct. 9, 2020.

(51) Int. Cl.
*A61F 2/72* (2006.01)
*A61F 4/00* (2006.01)
(Continued)

(52) U.S. Cl.
CPC ............. *A61H 1/0277* (2013.01); *A61F 2/72* (2013.01); *A61F 4/00* (2013.01); *A61F 5/013* (2013.01); *A61F 2002/5096* (2013.01); *A61F 2002/6854* (2013.01); *A61F 2002/6863* (2013.01); *A61F 2005/0155* (2013.01); *A61F 2005/0158* (2013.01); *A61H 2201/1638* (2013.01);
(Continued)

(58) Field of Classification Search
CPC ................. A61F 2005/0155; A61F 2005/0134
See application file for complete search history.

(56) References Cited

U.S. PATENT DOCUMENTS 5,547,464 A * 8/1996 Luttrell .................. A61H 1/024
                                                                482/111
6,872,187 B1   3/2005 Stark et al.
(Continued)

OTHER PUBLICATIONS

Written Opinion of the International Searching Authority dated Sep. 10, 2021, PCT/US2021/033629.

*Primary Examiner* — David H Willse
(74) *Attorney, Agent, or Firm* — Jacob M. Ward; Ward Law Office LLC

(57) ABSTRACT

An orthopedic system wherein a patient's brain is operably coupled to an actuation assembly for voluntarily moving a brace/limb of the patient between a number of desirable positions. An orthopedic brace, or one of more components thereof, which can be utilized with the orthopedic system.

27 Claims, 21 Drawing Sheets

(51) Int. Cl.
*A61F 5/01* (2006.01)
*A61H 1/02* (2006.01)
A61F 2/50 (2006.01)
A61F 2/68 (2006.01)

(52) U.S. Cl.
CPC ............... *A61H 2201/165* (2013.01); *A61H 2201/1676* (2013.01); *A61H 2201/501* (2013.01); *A61H 2230/605* (2013.01)

(56) References Cited

U.S. PATENT DOCUMENTS

| | | |
|---|---|---|
| 7,416,537 B1 | 8/2008 | Stark et al. |
| 8,460,222 B2 | 6/2013 | Garrec |
| 8,585,620 B2 | 11/2013 | McBean et al. |
| 2016/0287422 A1* | 10/2016 | Kelly ................... A61F 5/0127 |
| 2018/0177616 A1* | 6/2018 | Wang ....................... A61F 2/70 |
| 2018/0299971 A1* | 10/2018 | Eliasen ................ G06F 3/0219 |
| 2019/0216628 A1* | 7/2019 | Elias ...................... F16F 9/303 |
| 2020/0360169 A1 | 11/2020 | Kelly et al. |

\* cited by examiner

ORTHOPEDIC SYSTEM AND METHOD OF CONTROLLING THE SAME

CROSS-REFERENCE TO RELATED U.S. CASES

This application is a U.S. national counterpart application of international application serial No. PCT/US2021/033629 filed May 21, 2021, which claims priority to U.S. Provisional Patent Application No. 63/089,883, filed Oct. 9, 2020, the disclosures of which are hereby expressly incorporated by reference in their entireties.

BACKGROUND

This Orthopedic devices or braces are commonly used by medical professionals to help protect and/or rehabilitate the limb or joint of a patient post injury and/or post-surgery. In some situations such devices are utilized beyond just protecting and/or rehabilitation of a limb because the patient has completely and permanently lost the ability to actively control the function of the anatomical joint due to a traumatic injury or illness. For example, quadriplegic patients completely lose their ability to move a limb around a joint due to an injury that prevents, or significantly reduces, an operable interface between the brain and the muscles coupled to the bone components of the joint. In this situation the affected muscles are incapable of receiving a signal from the patient's brain to execute a desired movement. Unfortunately, in this scenario rehabilitation is not an option and an orthopedic system capable of being operably interfaced with a patient's brain so the patient can instruct the brace to execute a number of operations is desirable. For example, the patient desires to flex and extend their arm around the elbow joint. The ability to move their arm in this manner significantly enhances the patient's personal independence, and accordingly, their quality of life.

However, to achieve the enhancement of personal independence an orthopedic system should include the following characteristics: (i) a brace having appropriately coupled components, (ii) an actuator for moving the components of the brace, and (iii) a mechanism that provides an operable interface between the patient's brain and actuator so the patient can effectively communicate with the actuator and execute the instructed movement. Accordingly, an orthopedic system that includes the aforementioned characteristics is desirable, and particularly desirable for patients who have completely lost their ability to move a limb, e.g. a quadriplegic patient. However, current orthopedic systems suffer from a number of drawbacks in attempting to enhance a patient's independence in the above described manner.

For example, there are a number of orthopedic systems that utilize surgically implanted sensors to provide an operable interface between the patient's brain and the actuator. However, these systems come along with, for example, the cost and inherent risk associated with surgery. Furthermore, some systems utilize actuators that are activated by signals generated by the muscles that are operatively coupled to the joint of the damaged limb. In this case the damaged limb is positioned in the orthopedic brace and sensors are placed to detect signals from muscles surrounded by the brace. This type of arrangement requires the muscles within the brace to still be able to voluntarily contract so a signal can be sent to the actuator. This arrangement will not work with a patient who has lost an operable interface between the brain and the muscles since these muscles cannot voluntarily contract and generate a signal to activate an actuator. Current orthopedic systems also tend to be bulky, heavy, and complex which increases their cost and limits their ability to be worn under cloths. Furthermore, some of these systems require more than one sensor which further increases their complexity and cost.

Furthermore, the braces used in present orthopedic systems also have significant drawbacks. For example, these braces present fit and function challenges. In particular, present orthopedic braces are typically designed as a one-size fits all brace with a single-axle hinge joint that only allows the patient to move between extended and flexed positions. Such braces often have fit and alignment issues because the limb of the user, such as the arm, is not perfectly straight. For example, for most users the carrying angle of the arm may be about 5 degrees. Single-axle braces do not account for the carrying angle of the user's arm, which often causes the axis of the brace to be offset from the axis of the joint. As such, single-axle braces often limit the full range of motion of the user's joint because of the abnormal fit and alignment. The limited full range of motion may then hinder the use of the limb.

Additionally, common orthopedic braces do not allow pronation and supination movements of the arm. The lack of pronation and supination movements further minimizes the joint's range of motion.

Further, as discussed above, common orthopedic braces are passive braces that require movement from the user. The passive braces do not allow the user, such as patients with hemiplegia/paraplegia from a stroke, spinal cord injury, or other injury or illness, a sense of independence since such passive braces require movement from the patient or user.

The present disclosure generally relates to orthopedic systems with an operational interface between the patient's brain and an actuator for moving the brace. The present disclosure also generally relates to a brace with an increased range of motion for the patient.

SUMMARY

The present disclosure may comprise one or more of the following features and combinations thereof.

An orthopedic system having (i) a brace that includes a first component and a second component attached by a mechanical joint, (ii) an actuation assembly operably coupled to the first and second components so that activation of the actuation assembly causes movement of at least one of the components around the joint, (iii) a control unit interfaced with the actuation assembly so the control unit can send a signal to the actuation assembly, and (iv) a sensor operatively coupled to the control unit, the sensor capable of sensing a signal from a voluntary muscle contraction and then sending a signal to the control unit to activate the actuation assembly. In some embodiments the signal from the voluntary muscle contraction is above a predetermined threshold, e.g. 250 mV, to prevent causing the brace from inadvertently moving from a slight muscle twitch. The threshold can be altered as needed by the patient. In some embodiments, the brace includes a multi-axial joint extending between and interconnecting the first component and the second component of the brace. In another embodiment the multi-axial joint may be configured to rotate between a plurality of predetermined arrangements. In yet another embodiment the actuation assembly may be configured to move the first component and second component of the brace between the plurality of predetermined arrangements. The actuation assembly may include a first actuator coupled to the multi-axial joint and a second actuator coupled to the multi-axial joint.

A method of operating an orthopedic system having (i) a brace that includes a first component and a second component attached by a mechanical joint, (ii) an actuation assembly operably coupled to the first and second components so that activation of the actuation assembly causes movement of at least one of the components around the joint, (iii) a control unit interfaced with the actuation assembly so the control unit can send an instruction signal to the actuation assembly, and (iv) a sensor operatively coupled to the control unit, the sensor capable of sensing a signal from a voluntary muscle contraction and sending a signal to the control unit to activate the actuation assembly, the method includes the steps of: positioning the brace in contact with a limb of a patient wherein the limb has (i) a first bone component and a second bone component attached by an anatomical joint and (ii) at least one muscle operably coupled to the first bone component and/or second bone component but incapable of generating a signal; and positioning the sensor on the skin of the patient so the sensor can communicate with a muscle capable of generating a signal, wherein the muscle capable of generating a signal is spaced apart from the muscle incapable of generating a signal so that it is not operatively coupled to the first or second bone component. In one embodiment the sensor is an electromyography sensor (EMG sensor). In another embodiment the sensor is a mechanomyography sensor (MMG) sensor.

An orthopedic system having (i) a brace that includes a first component and a second component attached by a mechanical joint, (ii) an actuation assembly operably coupled to the first and second components so that activation of the actuation assembly causes movement of at least one of the components around the joint, (iii) a control unit interfaced with the actuation assembly so the control unit can send an instruction signal to the actuation assembly, and (iv) an extracorporeal device capable of signaling the control unit to actuate the actuation assembly.

In one embodiment the extracorporeal device is a computer. In another embodiment the extracorporeal device is capable of sending a digitized signal to the control unit. In some embodiments the signal sent from extracorporeal device is initiated via a bite stick operated by the patient.

A method of operating an orthopedic system having (i) a brace that includes a first component and a second component attached by a joint, (ii) an actuation assembly operably coupled to the first and second components so that activation of the actuation assembly causes movement of at least one of the components around the joint, (iii) a control unit interfaced with the actuation assembly so the control unit can send a signal to the actuation assembly, and (iv) a sensor operatively coupled to the control unit, the sensor capable of sensing movement of a body part of the patient and sending a signal to the control unit to actuate the actuation assembly, the method includes the steps of: positioning the brace in contact with a limb of a patient wherein the limb has (i) a first bone component and a second bone component attached by an anatomical joint and (ii) at least one muscle operably coupled to the first bone component and/or second bone component but incapable of contracting; and positioning the sensor relative to a body part so the sensor can sense movement of the body part and send a signal to the control unit. For example, the movement of the body part includes nodding the head, turning the head, moving the eyebrows, or any body part capable of being moved by the patient.

An orthopedic device adapted to be worn by a user may include an orthopedic brace, a detachable actuation assembly, and a control unit. The orthopedic brace may include an upper portion, a lower portion, and a multi-axial joint extending between and interconnecting the upper portion and the lower portion of the brace. The detachable actuation assembly may be selectively coupled to the brace to control actuation of the brace. The control unit may be coupled to the actuation assembly to direct actuation of the actuation assembly.

In some embodiments, the upper portion of the brace may be configured to be selectively attached to an upper portion of a limb of the user. The lower portion may be configured to be selectively attached to a lower portion of the limb of the user such that the multi-axial joint is proximate to a joint of the user between the upper and lower portions. The multi-axial joint may be configured to rotate between a plurality of predetermined arrangements.

In some embodiments, the detachable actuation assembly may be configured to move the upper and lower portions of the brace between the plurality of predetermined arrangements. The actuation assembly may include a first actuator coupled to the multi-axial joint and a second actuator coupled to the multi-axial joint.

In some embodiments, the first actuator may be configured to move the upper and lower portions brace in a flexion direction and an extension direction between the plurality of predetermined arrangements. The second actuator may be configured to move the upper and lower portions of the brace in a supination direction and a pronation direction between the plurality of predetermined arrangements.

In some embodiments, the control unit may be configured to selectively actuate the actuation assembly. The control unit may actuate the actuation assembly to move the orthopedic brace to a predetermined arrangement included in the plurality of predetermined arrangements in response to a signal associated with the predetermined arrangement.

These and other features of the present disclosure will become more apparent from the following description of the illustrative embodiments.

DETAILED DESCRIPTION OF THE DRAWINGS

Figures 1, 2:
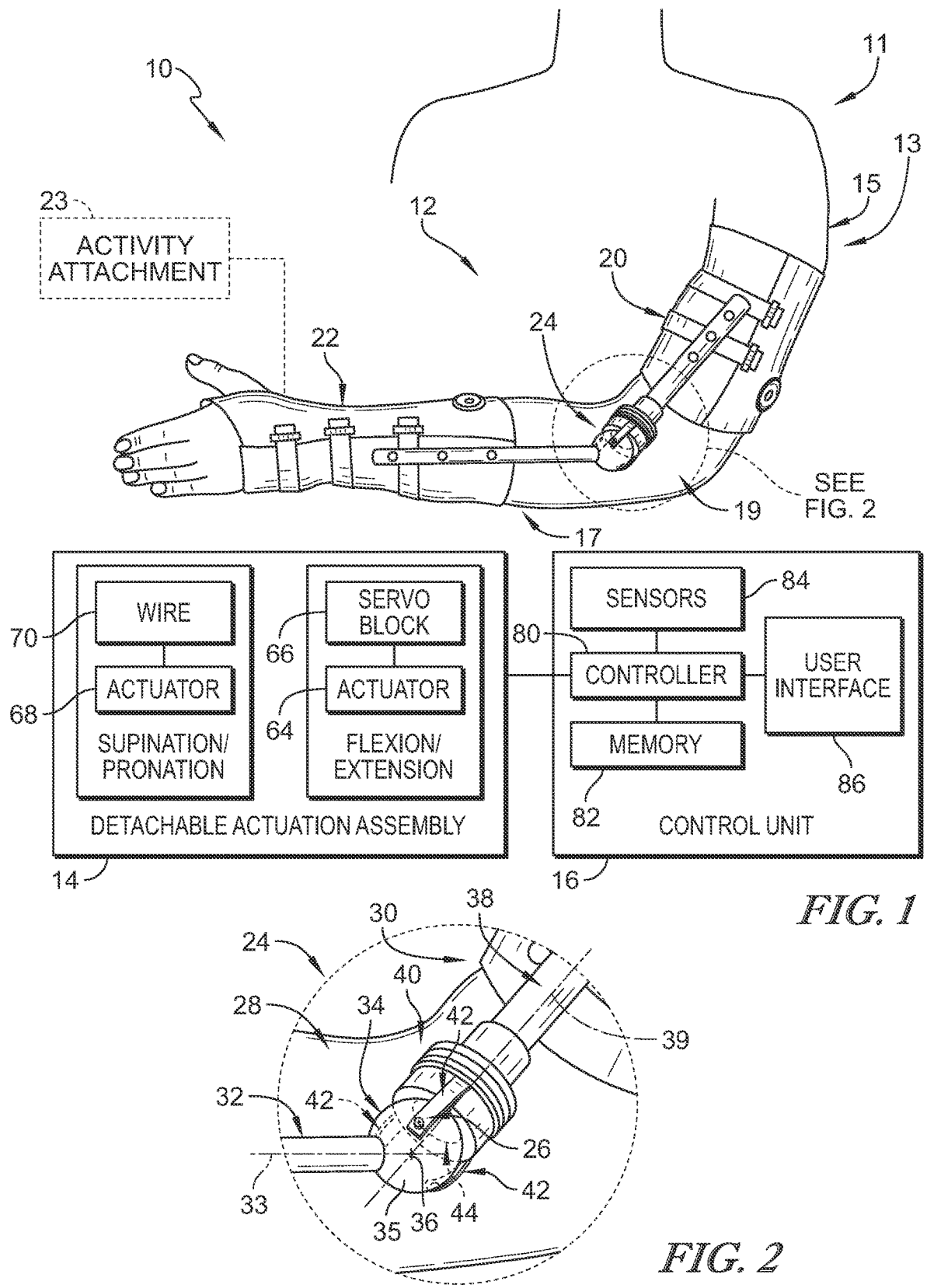
FIG. 1 is a diagrammatic and perspective view of a user wearing an orthopedic device adapted for protecting a joint of the user and aiding in rehabilitation of the joint showing the orthopedic device including an orthopedic brace having a multi-axial joint, a detachable actuation assembly configured to be selectively coupled to the orthopedic brace to move the brace between different arrangements, and a control unit coupled to the detachable actuation assembly and configured to control the actuation of motors included in the detachable actuation assembly.
FIG. 2 is a detailed view of the multi-axial joint included in the orthopedic brace of the orthopedic device of FIG. 1 showing the multi-axial joint is a ball and socket joint that extends between and interconnects upper and lower portions of the orthopedic brace.

For the purposes of promoting an understanding of the principles of the disclosure, reference will now be made to a number of illustrative embodiments illustrated in the drawings and specific language will be used to describe the same.

Figure 30:
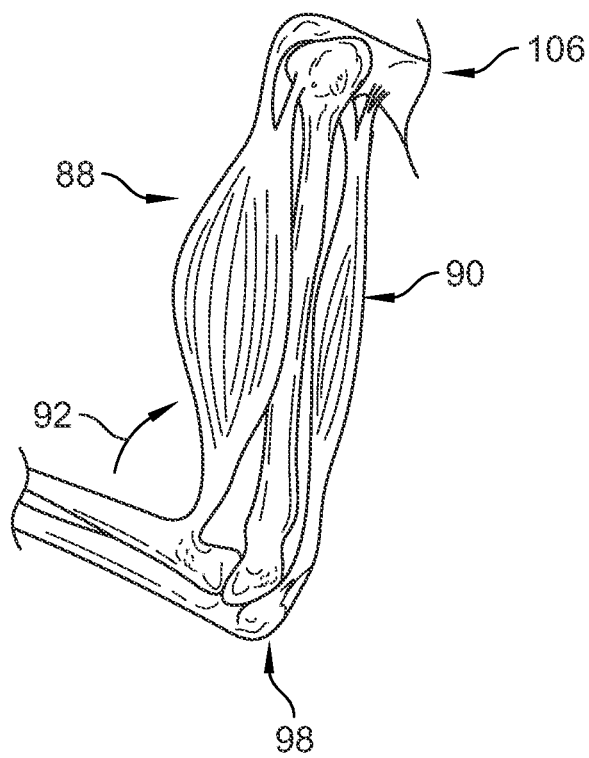
FIG. 30 illustrates an arm where the Biceps are contracted causing flexor.
Figure 31:
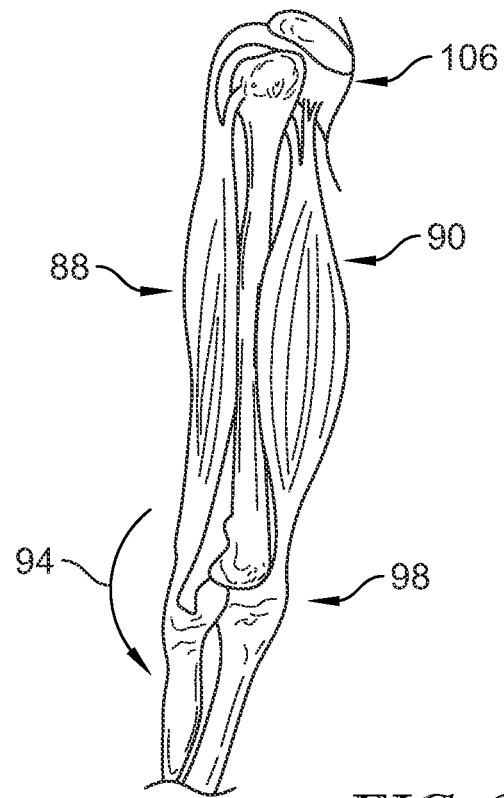
FIG. 31 shows the same arm as FIG. 30 but in this illustration the Triceps are contracted to cause extensor.

Under normal circumstances a limb will have muscle groups operatively coupled to bone components so that contraction of one muscle group will cause flexor of the limb around an anatomical joint of the limb, while contraction of the other muscle group will cause extensor of the limb around the joint. In a very simplistic view, the control of a healthy limb is governed by the brain of an individual sending signals to the muscle groups to cause contraction in an appropriate time/manner to cause flexor or extensor. This process is illustrated in FIGS. 30 and 31 as it relates to an arm 106. In particular, FIG. 30 illustrates the Biceps 88 receiving a signal from the brain to contract and thus causing the arm 106 to flexor around elbow 98 as indicated by arrow 92. While FIG. 31 illustrates the relaxation of the Biceps 88 and the contraction of the Triceps 90 as a result of receiving a signal from the brain thus causing extensor of the arm 106 around elbow 98 as indicated by arrow 94.

As previously discussed, an injury or disease can result in muscles losing their ability to voluntarily contract, e.g. quadriplegics, stroke victims, ALS. In these situations a person will lose voluntary control of a limb, e.g. an arm, and not be able to perform simple activities such as drinking water out of a container, being able to scratch their nose, or brush their teeth. So in order to execute these simple activities the person needs help from another individual/caretaker which significantly decreases their independence and quality of life.

This disclosure is directed to an orthopedic system that allows a patient to voluntarily instruct a brace to move a limb of a patient in a manner or predetermined manner, to perform a desired function, e.g. drink from a container.

Figure 32:
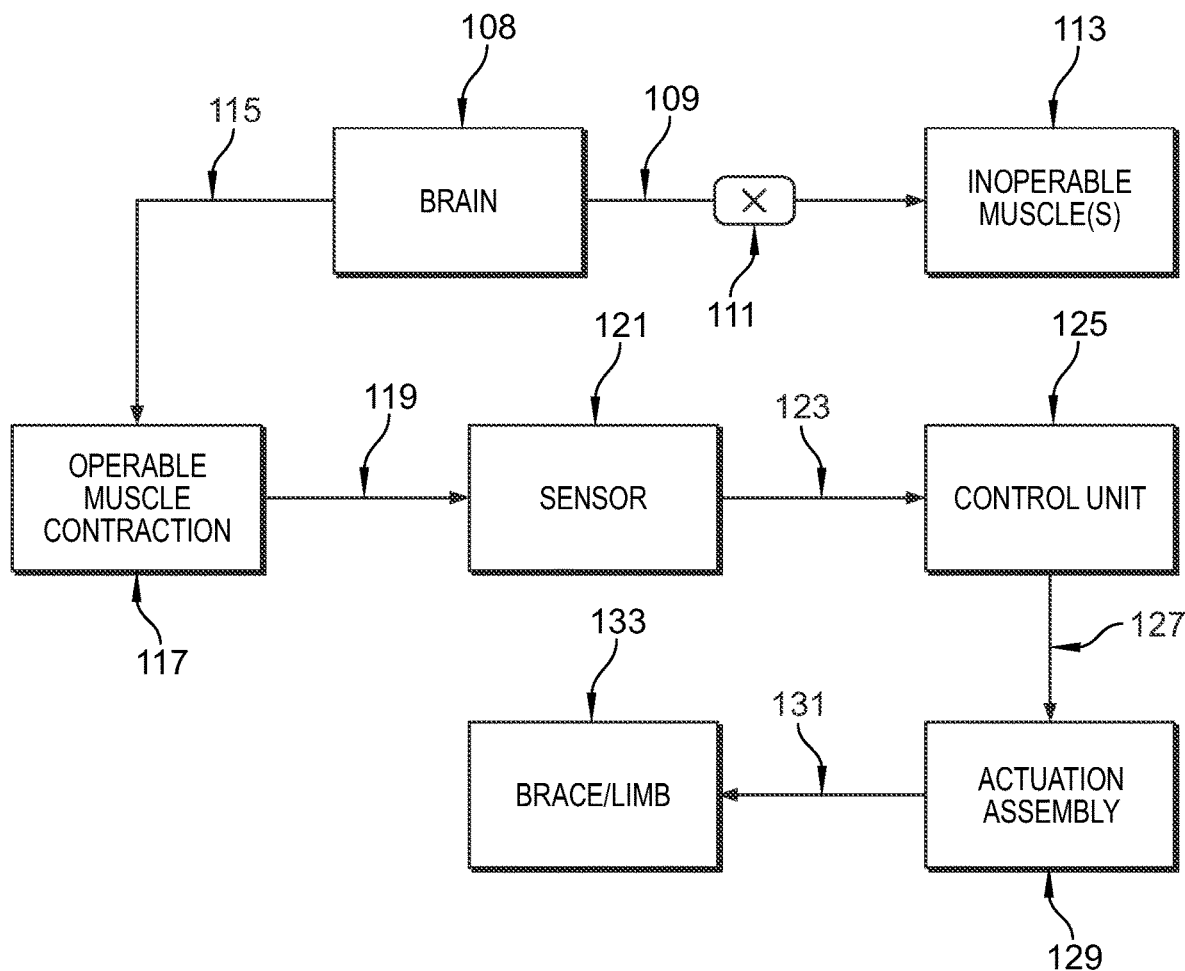
FIG. 32 shows a block diagram of the pathway for engaging or attempting to engage a muscle of a limb.

Now turning to FIG. 32 which shows a block diagram exemplifying a signal pathway for contracting, or attempting to contract, a muscle. For example, brain 108 of a patient suffering from quadriplegia may attempt to signal 109 and contract muscle(s) 113 to perform a desired task. However, as illustrated by indicia "X" 111, brain 108 is unable to initiate the contraction of muscle(s) 113 and the task cannot be completed.

However, a patient utilizing an embodiment of the present orthopedic system is able to bypass inoperable muscle(s) 113 by sending a signal 115 to an operable muscle(s) 117 as shown in FIG. 32. Upon receiving signal 115 muscle(s) 117 contracts thereby sending a second signal 119 to sensor 121 (e.g. EMG signal, MMG signal). Sensor 121 then communicates with control unit 125 via signal 123. Control unit 125 processes the signal 123 and relays instructions to actuation assembly 129 via signal 127, wherein actuation assembly 129 executes the instructions thereby moving brace/limb 133 in the appropriate manner (step 131).

Still referring to FIG. 32, one particular example of utilizing the above mechanism is one where the patient is suffering from quadriplegia and has lost the use of their arms. For example, rotation of the bone components around the elbow joint, i.e. bending of the elbow is lost. Here the sensor 121 is placed in communication with an operable muscle 117 such as the Trapezius muscle. When the patient desires to move an arm in a particular manner her/his brain 108 sends a signal 115 to an operable Trapezius muscle 117. As indicated above, upon receiving signal 115 the Trapezius muscle 117 contracts thereby sending an EMG signal 119 to sensor 121. Sensor 121 then communicates with the control unit 125 via the signal 123. Control unit 125 processes the signal 123 and relays instructions to the actuation assembly 129 via the signal 127. The actuation assembly 129 then executes the instructions which moves the brace/limb 133 around the elbow joint in accordance with the instructions received from the control unit 125 (step 131).

It should be appreciated that the instructions from the control unit 125 can include a number of movements. For example, the movements the brace/arm executes could be in accordance with the patient bringing a container of water to their mouth to drink water. The brace is equipped with a magnetic element and the container is also magnetic. In another situation, the movements could be in accordance with the patient wanting to scratch their nose or face. In yet another situation, the movements could be consistent with the patient wanting to "pick up" a bite stick and bring it to the patient's mouth where it could be used to interface with other devices. Again a magnetic element on the brace is used with a corresponding magnetic bite stick. In still another situation, the movements around the elbow joint would be consistent with straightening the arm to facilitate putting on a shirt.

In other embodiments the Trapezius muscle could be contracted a number of times, e.g. twice, by the patient to send two signals to the control unit 125 to instruct the actuation assembly 129, and thus the brace/arm 133, to execute a number of different movements.

While the orthopedic system of the present disclosure only needs a single sensor to operate, it could also be operated with more than one sensor. For example, a first sensor could be placed in communication with the Trapezius muscle and a second sensor placed in communication with another operable muscle 117, such as the Deltoid muscle. In this embodiment the patient could contract the Trapezius muscle followed by the contraction of the Deltoid muscle. The sequential signals sent to the control unit 125 from two separate muscles are processed to drive the actuation assembly 129 to move the brace/arm in yet another set of movements. Another embodiment is where the operable muscle 117 sends differentiated signals to the sensor based upon the intensity of the contraction of the muscle, or the length of time the muscle is contracted, each one representing a desired movement of the arm. The system of the present disclosure can also include a number of actuation assemblies to move the limb in a more complex manner.

Figure 33:
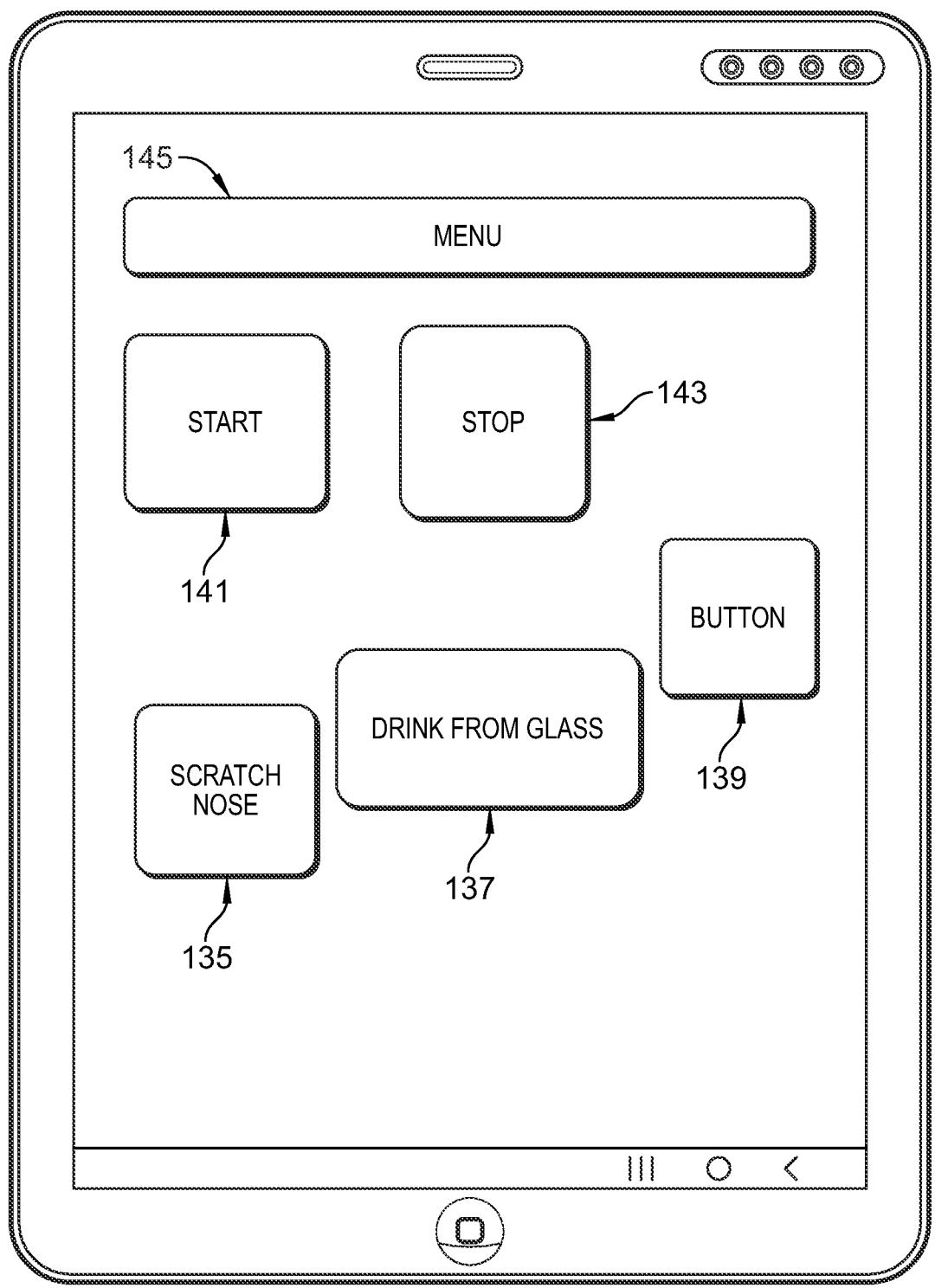
FIG. 33 is an illustration of an iPad with several icons a patient can touch to initiate movement of a limb utilizing the orthopedic system discussed herein.

In yet another embodiment, the orthopedic system of the disclosure can be utilized in cooperation with an extracorporeal device capable of signaling the control unit 125 to actuate the actuation assembly 129. In one embodiment the extracorporeal device is a computer capable of sending a signal to the control unit 125 to activate the actuation assembly 129. For example, FIG. 33 shows an iPad displaying several icons labeled with different movement actions. Specifically, icon 145 is labeled "menu", icon 141 "start", 143 "stop", 135 "Scratch Nose", 137 "Drink from Glass". In one embodiment a patient can utilize a bite stick to press icon 145 which then shows a number of actions on the iPad screen. Then the patient can choose a desirable action from the icons. In particular, the patient my select the "Drink from Glass" icon and press it with a bite stick, which causes the iPad to send a signal(s) to the control unit 125 which then instructs the actuation assembly 129 to move the brace/arm consistent with those for drinking from a magnetic container. Pressing the other icons will cause the brace/arm to move in a manner consistent with the label. It should be appreciate that any signal from any extracorporeal device can be utilized to communicate with the control unit 125, with the appropriate signal, for example a digital or analog signal.

Any combination of the above movements or methods of signaling the actuator to move the brace/arm in a particular manner are within the scope of the present disclosure. These examples are not limiting, but are described to illustrate the orthopedic system's broad scope of abilities for assisting a patient.

The above discussed orthopedic system can be utilized with braces currently on the market. The below discussion is directed to a brace, or components thereof in any combination, that can also be utilized in the orthopedic system of the present disclosure.

Figure 3:
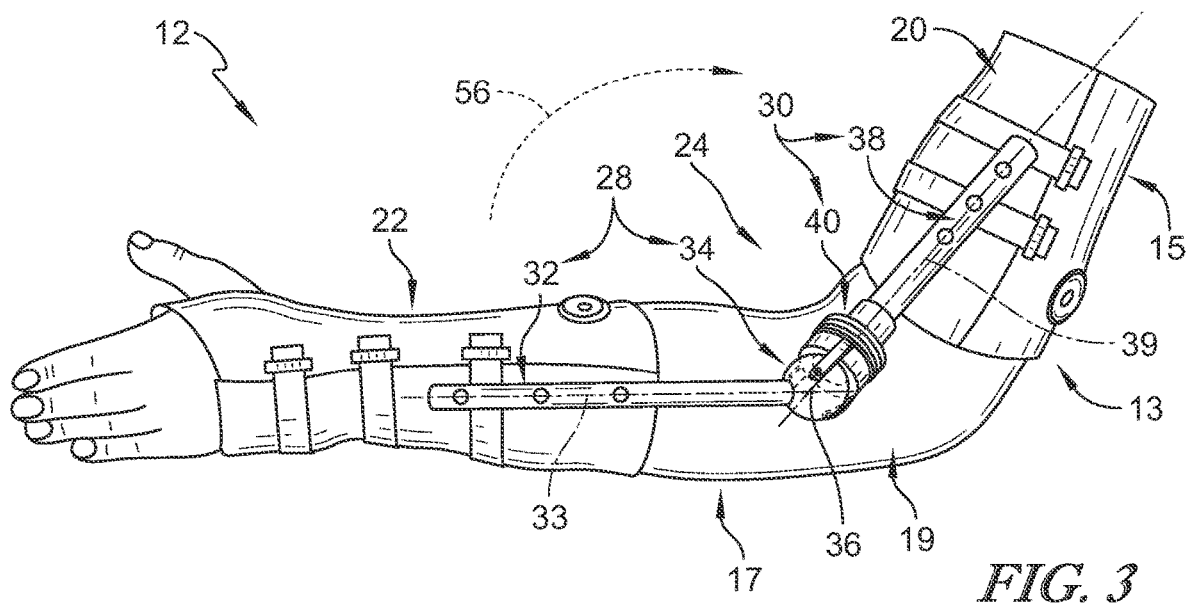
FIG. 3 is a perspective view of the orthopedic device of FIG. 1 in which the multi-axial joint of the orthopedic brace is in an extended arrangement.
Figure 4:
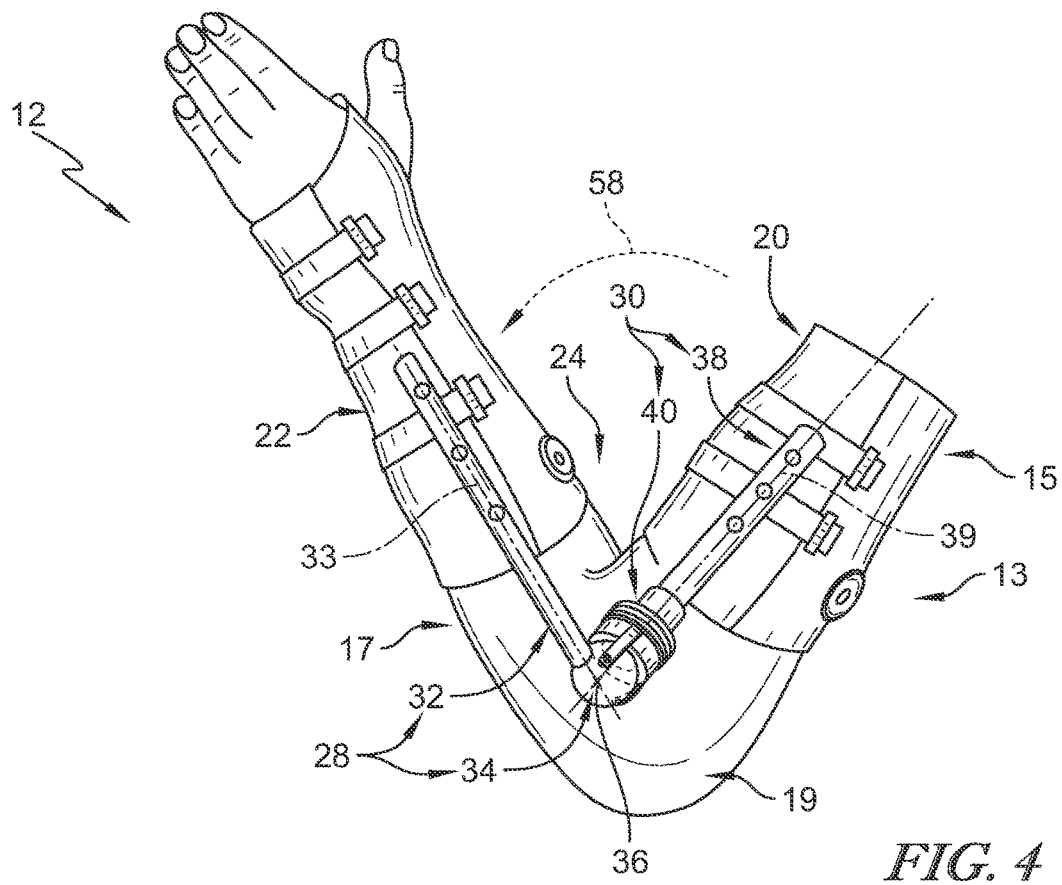
FIG. 4 is a view similar to FIG. 3 in which the multi-axial joint of the orthopedic brace has moved from the extended arrangement to a flexed arrangement.
Figure 6:
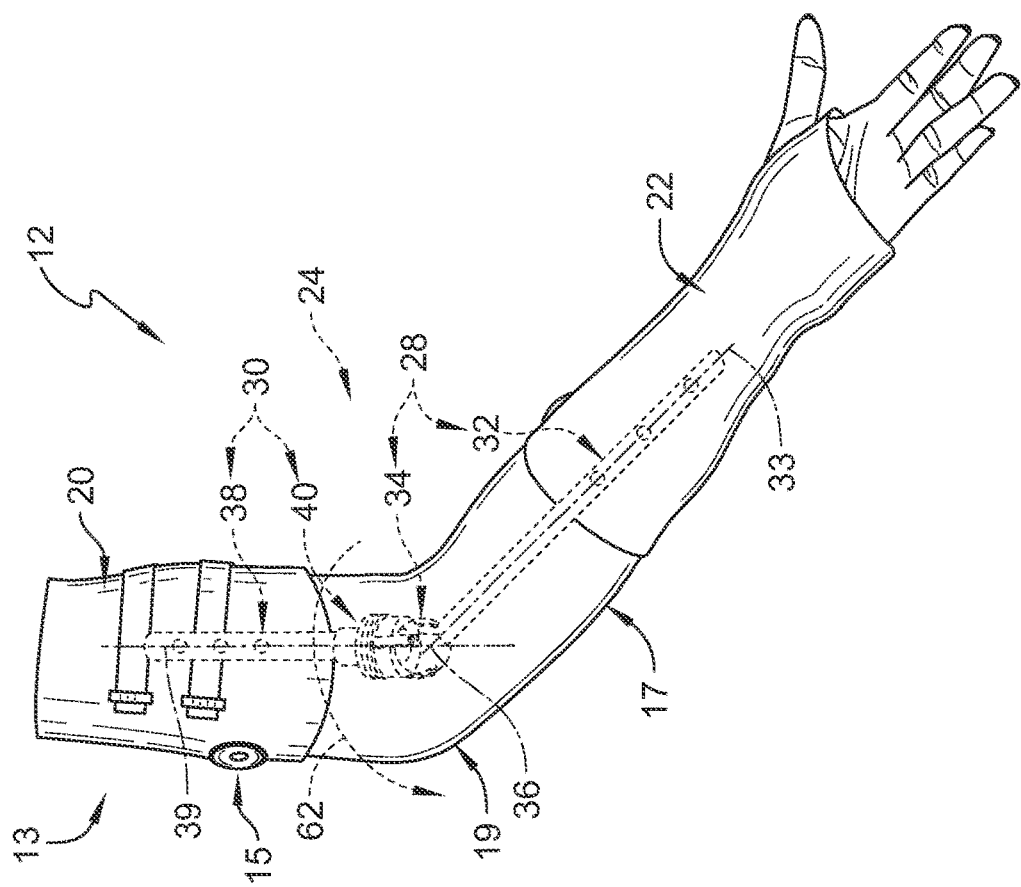
FIG. 6 is a view similar to FIG. 5 in which the multi-axial joint of the orthopedic brace has moved from the pronated arrangement to a supinated arrangement.
Figure 5:
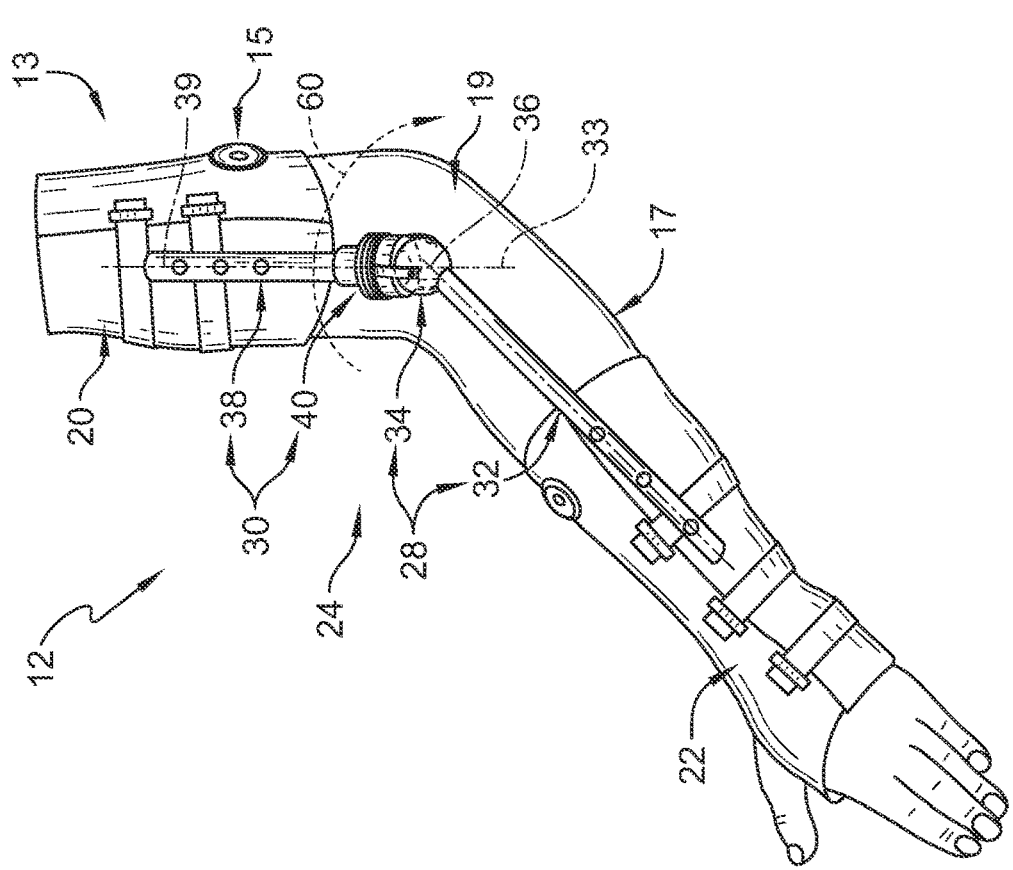
FIG. 5 is a diagrammatic and perspective view of the orthopedic device of FIG. 1 in which the multi-axial joint of the orthopedic brace is in a pronated arrangement.
Figure 8:
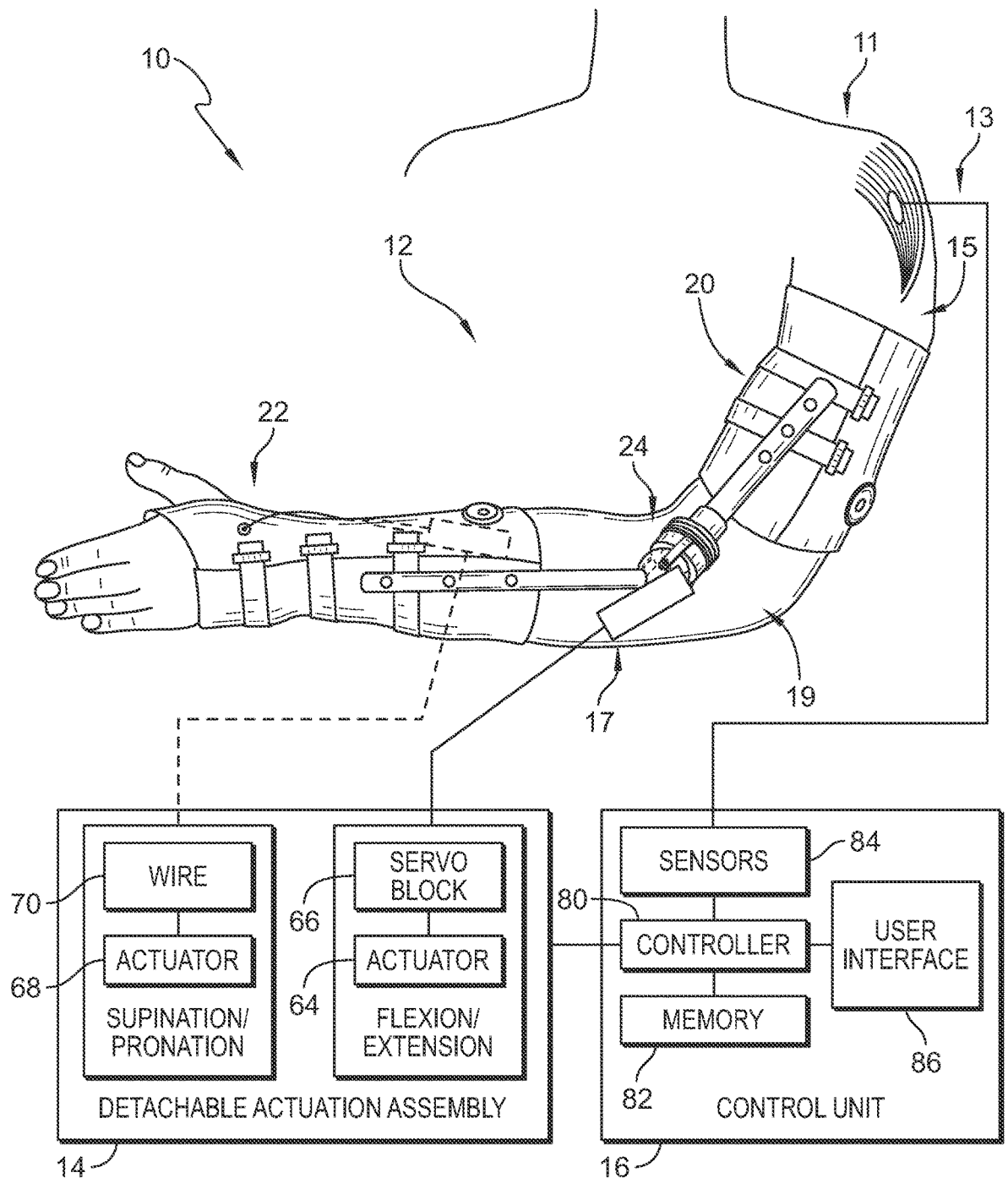
FIG. 8 is a diagrammatic and perspective view of the orthopedic device of FIG. 1 showing the detachable actuation assembly assembled on the orthopedic brace.

An illustrative orthopedic device 10 adapted to be worn by a patient or user 11 is shown in FIG. 1. The orthopedic device 10 includes an orthopedic brace 12, detachable actuation assembly 14, and a control unit 16 as shown in FIGS. 1-2 and 8. The orthopedic brace 12 is configured to be worn by the user 11, in particular on an arm 13 of the user 11, to provide protection for the user's elbow joint 19. In the illustrative embodiment, the orthopedic brace 12 has a multi-axial joint proximate to the joint 19 of the user 11 that allows the brace 12 to rotate between a plurality of arrangements. The plurality of arrangements include an extended arrangement as shown in FIG. 3, a flexed arrangement as shown in FIG. 4, a pronated arrangement as shown in FIG. 5, and a supinated arrangement as shown in FIG. 6. It should be understood that the embodiments of the brace 12 described herein can include a uniaxial joint as opposed to a multiaxial joint, or a combination of a multi-axial joint and a uniaxial joint.

The detachable actuation assembly 14 is configured to be selectively coupled to the brace 12 to move the multi-axial joint 24 between the extended, flexed, pronated, and supinated arrangements. The control unit 16 is coupled to the actuation assembly 14 and is configured to control the actuation of actuators 64, 68 included in the actuation assembly 14 to cause the actuators 64, 68 to move the brace 12 between the extended, flexed, pronated, and supinated arrangements.

Commonly used orthopedic braces include a single-axle hinge joint that only allows the user to move between an extended arrangement and a flexed arrangement. Such braces often have abnormal fit and alignment issues because the arm 13 of the user 11 is not completely straight.

Figure 29:
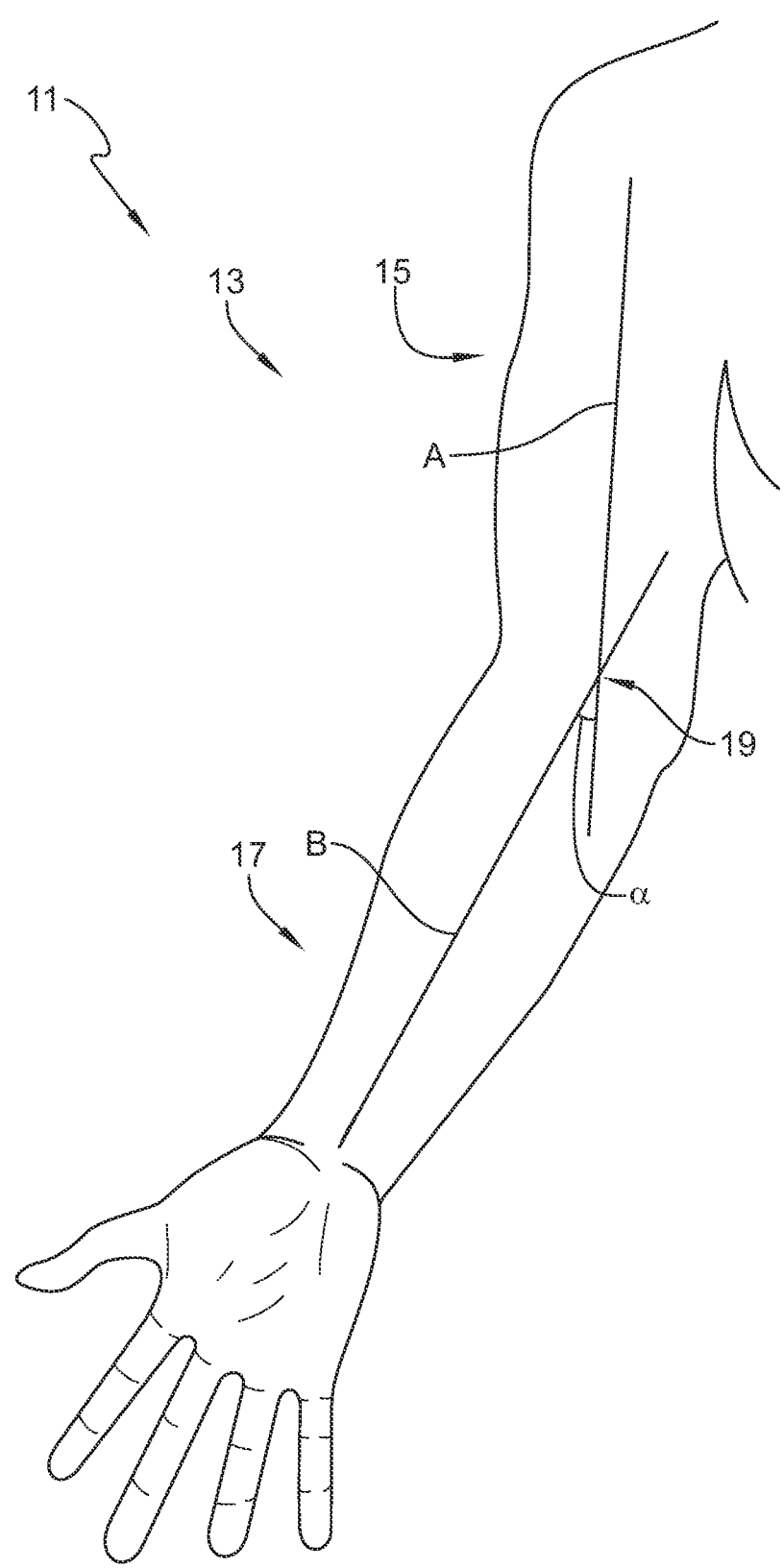
FIG. 29 is an elevation view of an arm of the user showing the carrying angle of the arm.

For example, the elbow 19 has a carrying angle a as shown in FIG. 29. The arm 13 of the user 11 has an upper arm axis A that runs along the humerus of the upper arm 15 and a forearm axis B that runs along the forearm 17. At the intersection of the upper arm axis A and the forearm axis B, the forearm axis B is angularly offset from the upper arm axis A, which forms the carrying angle a. For most users the carrying angle a may be about 5 degrees.

Single-axle braces do not account for the carrying angle a of the user's arm 13, which often causes the hinge axis of the brace 12 to be offset from the axis of the elbow joint 19. As such, single-axle braces often limit the full range of motion of the user's elbow joint 19 because of the abnormal fit and alignment issues. The limited full range of motion may hinder the rehabilitation of the user's elbow joint 19.

To reduce fit and alignment issues and improve the overall range of motion of the user 11 while wearing the device 10, the device 10 includes the multi-axial joint 24 configured to allow the brace 12 to move between the plurality of different arrangements including the extended, flexed, pronated, and supinated arrangements as shown in FIGS. 3-6. The multi-axial joint 24 has a flexion/extension angle 25 between the upper and lower portions 20, 22 and a supination/pronation angle 27A, 27B between the upper and lower portions 20, 22. The multi-axial joint 24 allows a maximum flexion/extension angular displacement of about 150 degrees in the flexion/extension directions. The multi axial joint allows a maximum supination/pronation angular displacement of about 140 degrees.

Even still, common orthopedic braces, such as the single-axle hinge joint braces, are passive and require movement of the user 11 to flex and extend the limb 13. These passive braces do not allow the user 11 a sense of independence since such passive braces require the user 11 to flex and/or extend the elbow joint 19.

The detachable actuation assembly 14 is configured to provide varying levels of assistance to the user 11 to move the brace 12 between the different arrangements. The detachable actuation assembly 14 includes the different actuators 64, 68 that are configured to move the brace 12 between the different arrangements. In some embodiments, both actuators 64, 68 may be coupled to the brace 12 at once. In other embodiments, one actuator 64, 68 may be coupled to the brace 12, while the other is detached while not in use.

Depending on the user's rehabilitation schedule, the detachable actuation assembly 14 may be detached to reduce the weight of the brace 12 during everyday activities or attached for assistance during rehabilitation activities. The actuation assembly 14 may assist the user during rehab by changing the resistance of the actuators 64, 68 to make the activities easier or more difficult. The actuation assembly 14 is easily detachable to also recharge the actuators 64, 68.

The detachable actuation assembly 14 may also aid users 11 who have suffered hemiplegia or paraplegia from a stroke or other type of injury or illness. Such users 11 may have some, if not all, function of the limb 13. The detachable actuation assembly 14 provides assistance to move the limb 13 between the different arrangements for different activities, like drinking a glass of water, which would help the user 11 regain some sense of independence in their everyday life.

The detachable actuation assembly 14 and control unit 16 are also configured to allow the doctor or physician to better assist the user 11 in rehabilitation. The detachable actuation assembly 14 may allow the physician to move the brace 12 through different rehab activities from a separate location. The doctor may be able to monitor the user 11 while the user 11 is at home.

The control unit 16 is pre-programmed with different activities or motions. The pre-programmed activities may be selected by the user 11 using sensors 84 included in the control unit 16 or through the use of a user interface 86.

Turning again to the orthopedic brace 12, the orthopedic brace 12 includes an upper portion 20, a lower portion 22, and the multi-axial joint 24 extending between and interconnecting the upper portion 20 and the lower portion 22 of the brace 12 as shown in FIGS. 1-15. The upper portion 20 of the brace 12 is configured to be selectively attached to the upper portion 15 of the user's limb 13, while the lower portion 17 is configured to be selectively attached to the lower portion 17 of the user's limb 13. The upper and lower portions 20, 22 are attached to the upper and lower portions 15, 17 of the limb 13 such that the multi-axial joint 24 is proximate to the elbow joint 19 of the user 11 between the upper and lower portions 20, 22.

The upper and lower portions 20, 22 are braces 20, 22 that are adapted to be strapped to the upper or lower arm 15, 17 of the user 11. The upper and lower portions 20, 22 may be made from different wearable fabric or other structural materials so that multi-axial joint 24 may be coupled to the upper and lower portions 20, 22.

The upper and lower portions 20, 22 are strapped to the upper arm 15 and the lower arm 17 of the user 11 using a strapping apparatus. In the illustrative embodiments, the strapping apparatus includes straps that tighten the braces 20, 22 to the arm 13 of the user 11. In other embodiments, the strapping apparatus may be a BOA system configured to tighten or loosen the brace on the corresponding portion 15, 17 of the arm 13.

In other embodiments, the upper and lower portions 20, 22 may be another suitable brace that the user 11 may wear so that the multi-axial joint 24 may be coupled proximate to the joint 19 of the user 11. The strapping apparatus may be another suitable attachment method to secure the portions 20, 22 in place on the user's arm 13.

In the illustrative embodiment, the multi-axial joint 24 is a ball and socket joint 24 as shown in FIGS. 1-7 and 9-14. The ball and socket joint 24 includes a rotatable ball portion 28 and a socket portion 30 that forms a ball socket 44 to receive the rotatable ball portion 28.

The rotatable ball portion 28 includes a ball arm 32 that extends along a center ball axis 33 and a ball 34 as shown in FIGS. 2-7 and 9-14. The ball arm 32 is coupled to the lower portion 22 of the orthopedic brace 12. The ball 34 is coupled to one end of the ball arm 32 with a center 36 located on the center axis 33 of the ball arm 32.

The socket portion 30 includes a socket arm 38 that extends along a center socket axis 39 and a socket housing 40 as shown in FIGS. 2-7 and 9-14. The socket arm 38 is coupled to the upper portion 20 of the orthopedic brace 12. The socket housing 40 is coupled to one end of the socket arm 38.

Figure 7:
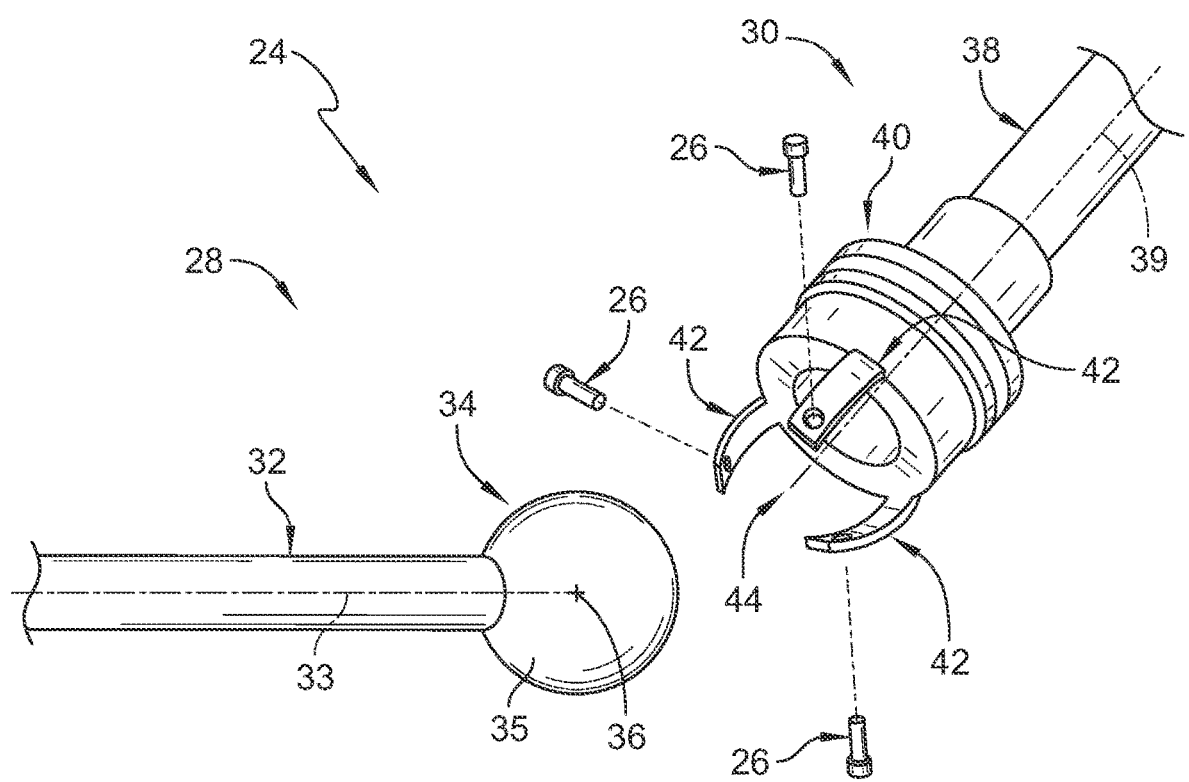
FIG. 7 is an exploded view of the multi-axial joint of the orthopedic device of FIG. 1 showing the orthopedic device further including a locking assembly configured to block rotation of the ball in the ball socket so that the orthopedic brace is locked into a predetermined position.

The socket housing 40 forms the ball socket 44 as shown in FIG. 7. The ball 34 is located in the ball socket 44 to couple the rotatable ball portion 28 to the socket portion 30 and from the multi-axial joint 24. The ball 34 is free to rotate about the center 36 in the ball socket 44.

In the illustrative embodiments, the socket housing 40 includes three prongs 42 as shown in FIG. 7. The prongs 42 form the ball socket 44 of the socket housing 40 such that the prongs 42 extend partially around the ball 34 when the ball 34 is in the ball socket 44. The prongs 42 are compliant so that the ball 34 may be inserted into the ball socket 44.

In the illustrative embodiment, the socket housing 40 includes three prongs 42. In some embodiments, the socket housing 40 may include only two prongs 42. In other embodiments, the socket housing 40 may include more than three prongs 42.

Figure 10:
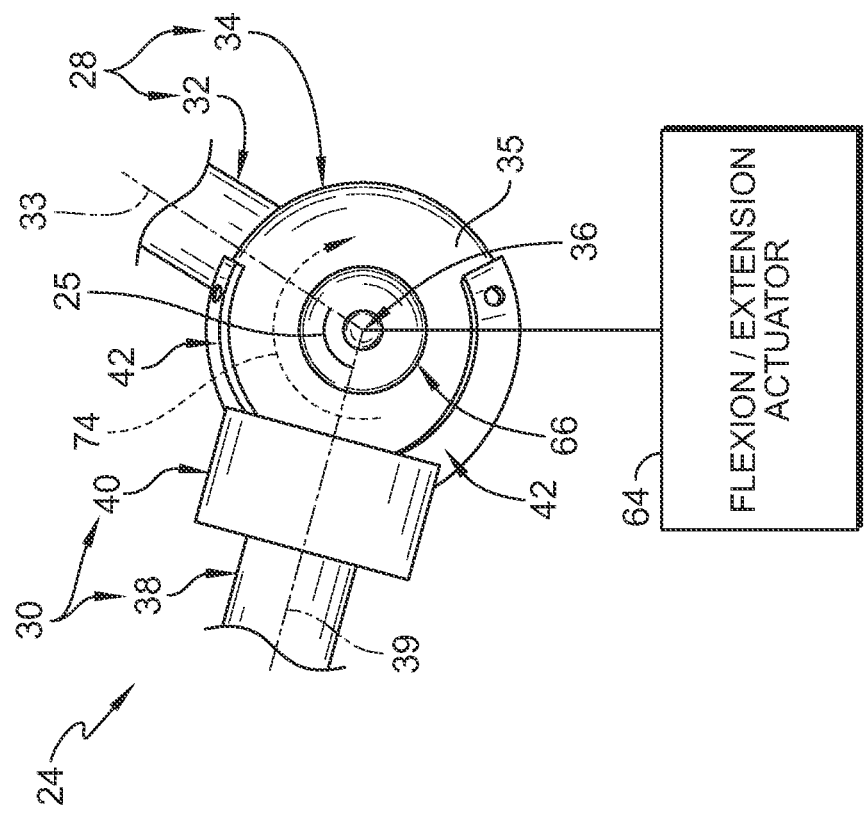
FIG. 10 is a view similar to FIG. 9 in which the actuation assembly has been engaged to move to a second position to cause the multi-axial joint of the orthopedic brace to move from the extended arrangement to the flexed arrangement.
Figure 9:
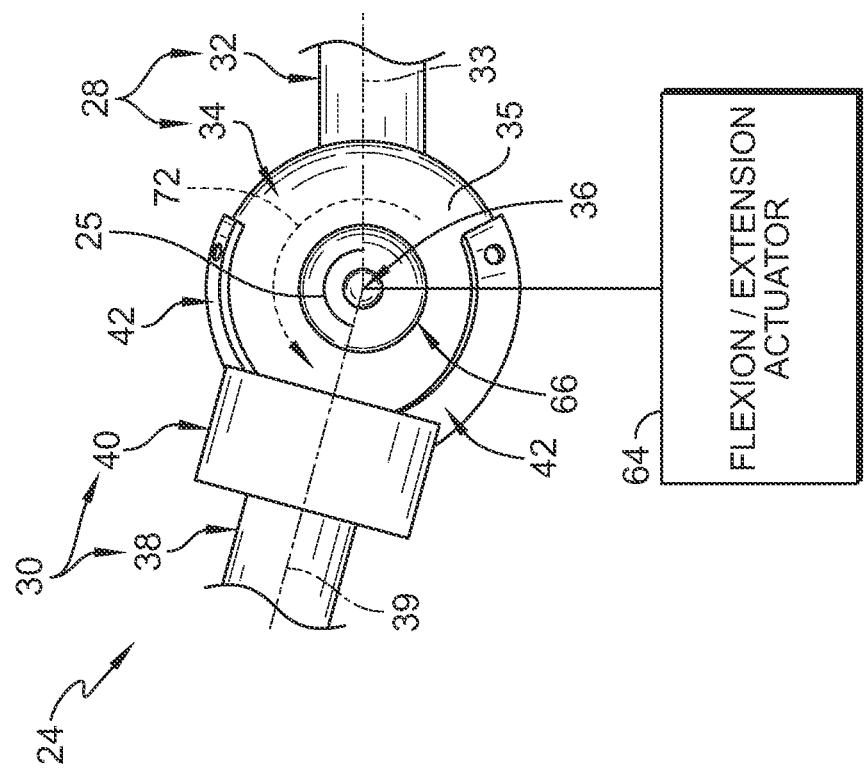
FIG. 9 is a diagrammatic elevation view of the multi-axial joint included in the orthopedic device of FIG. 8 showing the actuation assembly in a first position to cause the multi-axial joint of the orthopedic brace to be in the extended arrangement.
Figure 14:
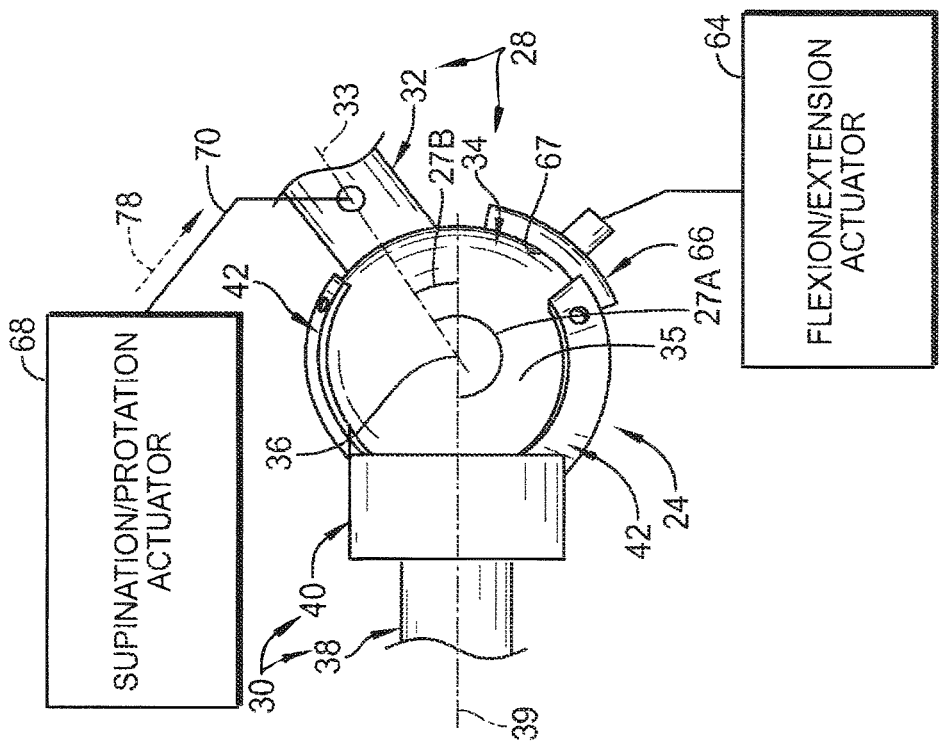
FIG. 14 is a view similar to FIG. 13 in which the actuation assembly has been engaged to move to the second linear position to cause the multi-axial joint of the orthopedic brace to move from the pronated arrangement to the supinated arrangement.
Figure 13:
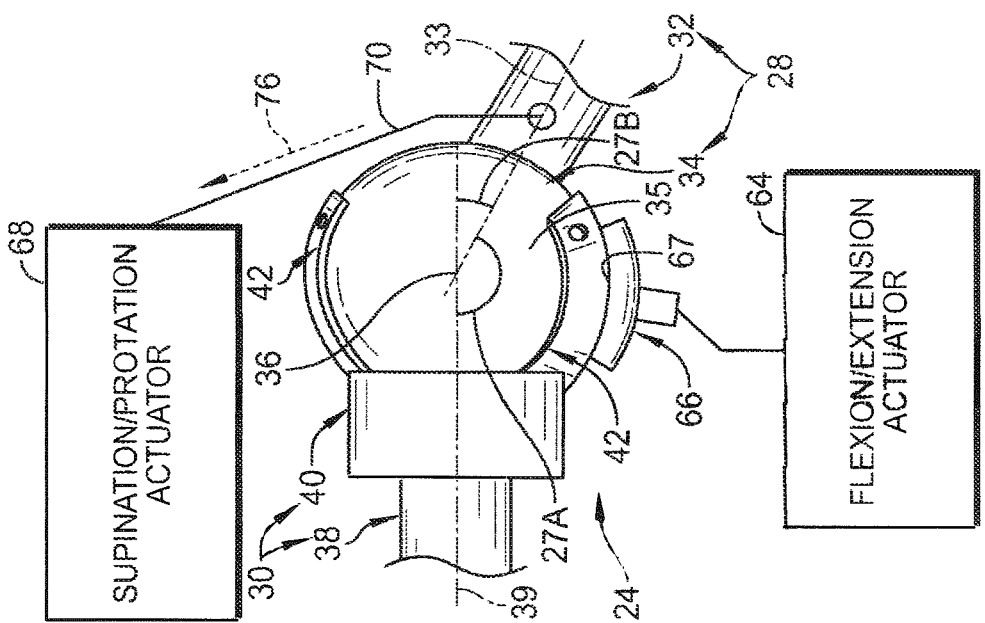
FIG. 13 is a diagrammatic aerial view of the orthopedic device of FIG. 8 showing the actuation assembly in the first linear position and coupled to the multi-axial joint of the orthopedic brace in the pronated arrangement.
Figure 15:
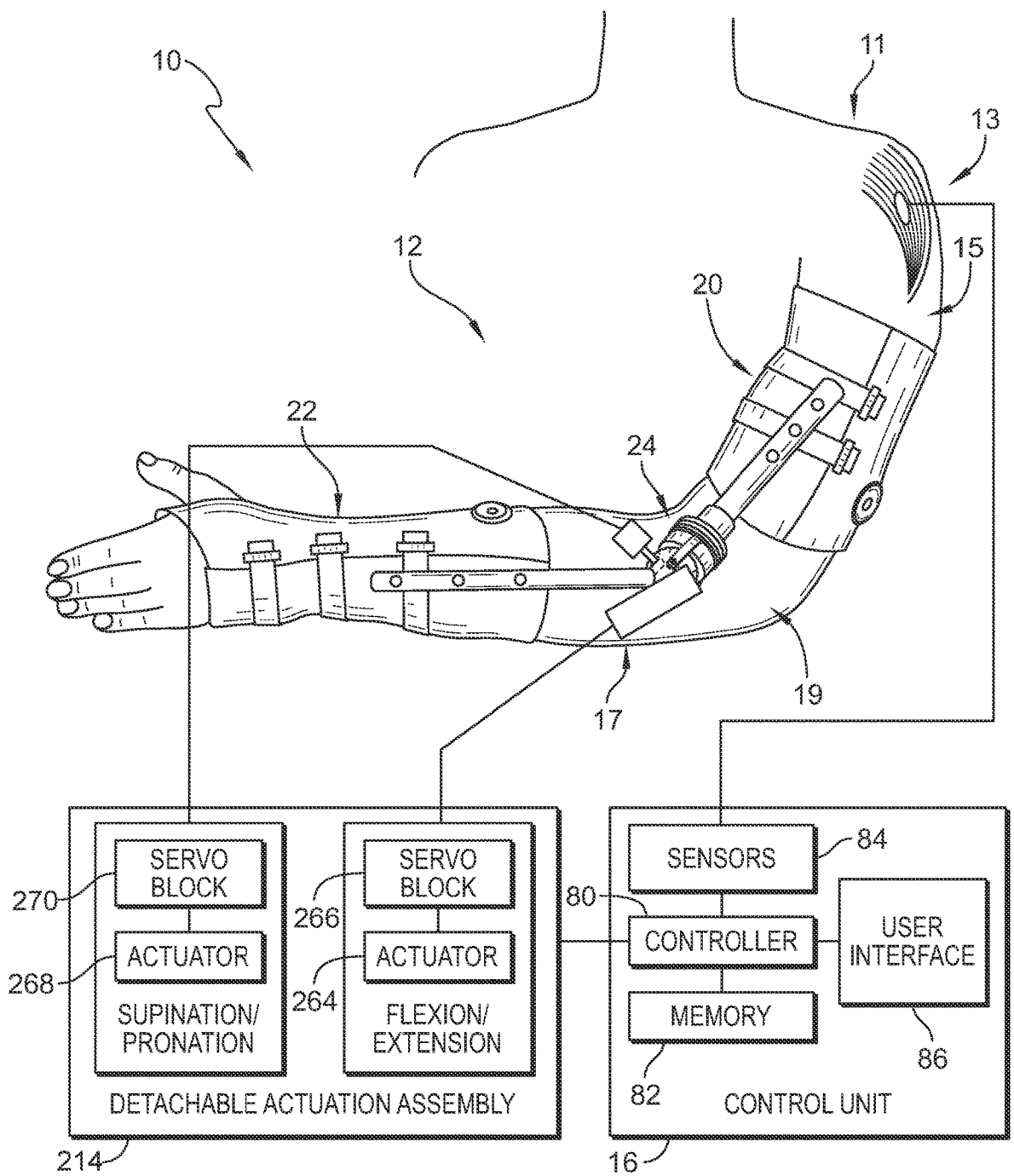
FIG. 15 is another embodiment of the detachable actuation assembly included in the orthopedic device of FIG. 1 showing the actuation assembly includes two servo motors that are coupled directly to the multi-axial joint of the brace.
Figure 16:
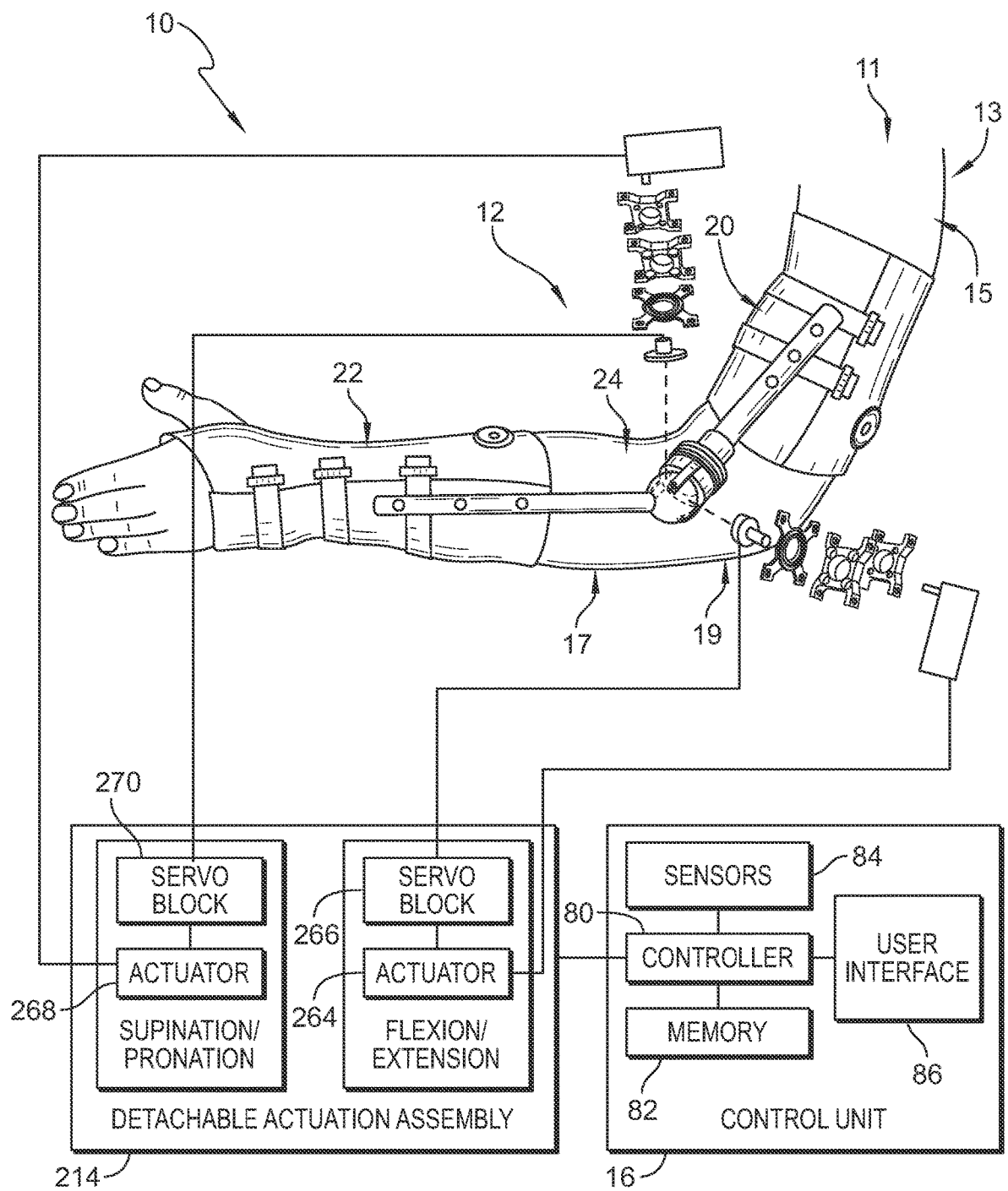
FIG. 16 is a diagrammatic and exploded view of the orthopedic device of FIG. 15 showing the actuation assembly further includes a first actuator block that couples the first actuator to the multi-axial joint to move the multi-axial joint in the flexion and extension directions and a second actuator block that couples the second actuator to the multi-axial joint to move the multi-axial joint in the pronation and supination directions.

The flexion/extension angle 25 of the multi-axial joint 24 is between the center ball axis 33 and the center socket axis 39 as shown in FIGS. 9 and 10. The supination/pronation angles 27A, 27B are between the center ball axis 33 and the center socket axis 39 as shown in FIGS. 13 and 14.

The orthopedic brace 12 further includes a locking assembly 26 as shown in FIG. 7. The locking assembly 26 is configured to engage the ball 34 of the ball and socket joint 24 to block rotation of the ball 34 in the ball socket 44 of the housing 40.

In the illustrative embodiment, the locking assembly 26 is a set screw 26. The set screw 26 is configured to extend through one of the three prongs 42 and engage an outer surface 35 of the ball 34. The set screw 26 has threads that mate with the prong 42 so that the set screw 26 may be tightened/loosened to engaged the ball 34.

To lock the ball 34 in the ball socket 44, the set screw 26 is screwed in or tightened thereby increasing contact with the ball 34. To unlock the ball 34 and to allow it to rotate about the ball socket 44, the set screw 26 is unscrewed to disengage the set screw 26 from the ball 34.

The multi-axial joint 24 is configured to move between a plurality of predetermined arrangements that include the extended arrangement as shown in FIG. 3, the flexed arrangement as shown in FIG. 4, the pronated arrangement as shown in FIG. 5, and the supinated arrangement as shown in FIG. 6. The plurality of predetermined arrangements includes a plurality of arrangements between the extended, flexed, pronated, and supinated arrangements. The multi-axial joint 24 is configured to move in a flexion direction as indicated by arrow 56, an extension direction as indicated by arrow 58, a pronation direction as indicated by arrow 60, and a supination direction as indicated by arrow 62 between the plurality of predetermined arrangements as suggested in FIGS. 3-6.

The multi-axial joint 24 moves in the flexion direction 56 when changing from the extended arrangement to the flexed arrangement. Conversely, the multi-axial joint 24 moves in the extension direction 58 when changing from the flexed arrangement to the extended arrangement.

The multi-axial joint 24 moves in the supination direction 62 when changing from the pronated arrangement to the supinated arrangement. Conversely, the multi-axial joint 24 moves in the pronation direction 60 when changing from the supinated arrangement to the pronated arrangement.

The locking assembly 26 allows the multi-axial joint 24 to be locked in any one of the plurality of predetermined arrangements. Being able to lock the brace 12 in several different arrangements is helpful during rehabilitation of an injured joint 19.

The multi-axial joint 24 is also configured to move in multiple directions 56, 58, 60, 62 at the same time. In other words, the multi axial joint 24 is configured to rotate in the extension direction 58 and the pronation direction 60 at the same time. Similarly, the multi-axial joint 24 is configured to rotate in the flexion direction 56 and the supination direction 62 simultaneously, the extension direction 58 and the supination direction 62 simultaneously, or the flexion direction 56 and the pronation direction 60 simultaneously. As such, the multi-axial joint 24 allows a larger range of motion compared to single-axial hinge braces. The multi-axial joint 24 is also configured to move/adjust in a lateral directions to account for the carrying angle-& of the user 11.

In some embodiments, the lower portion 22 of the brace 12 may include an activity attachment 23 as shown in FIG. 1. The activity attachment 23 may be selectively coupled to the lower portion 22 of the brace 12. The activity attachment 23 may be configured to help the user 11 to different tasks, such as drinking, eating, itching, etc. In some embodiments, the activity attachment 23 may be a grabber to attach a cup for drinking or hold utensils for eating. In other embodiments, the activity attachment 23 may be a nose itching device to aid the patient or user 11 in itching their nose.

Figures 11, 12:
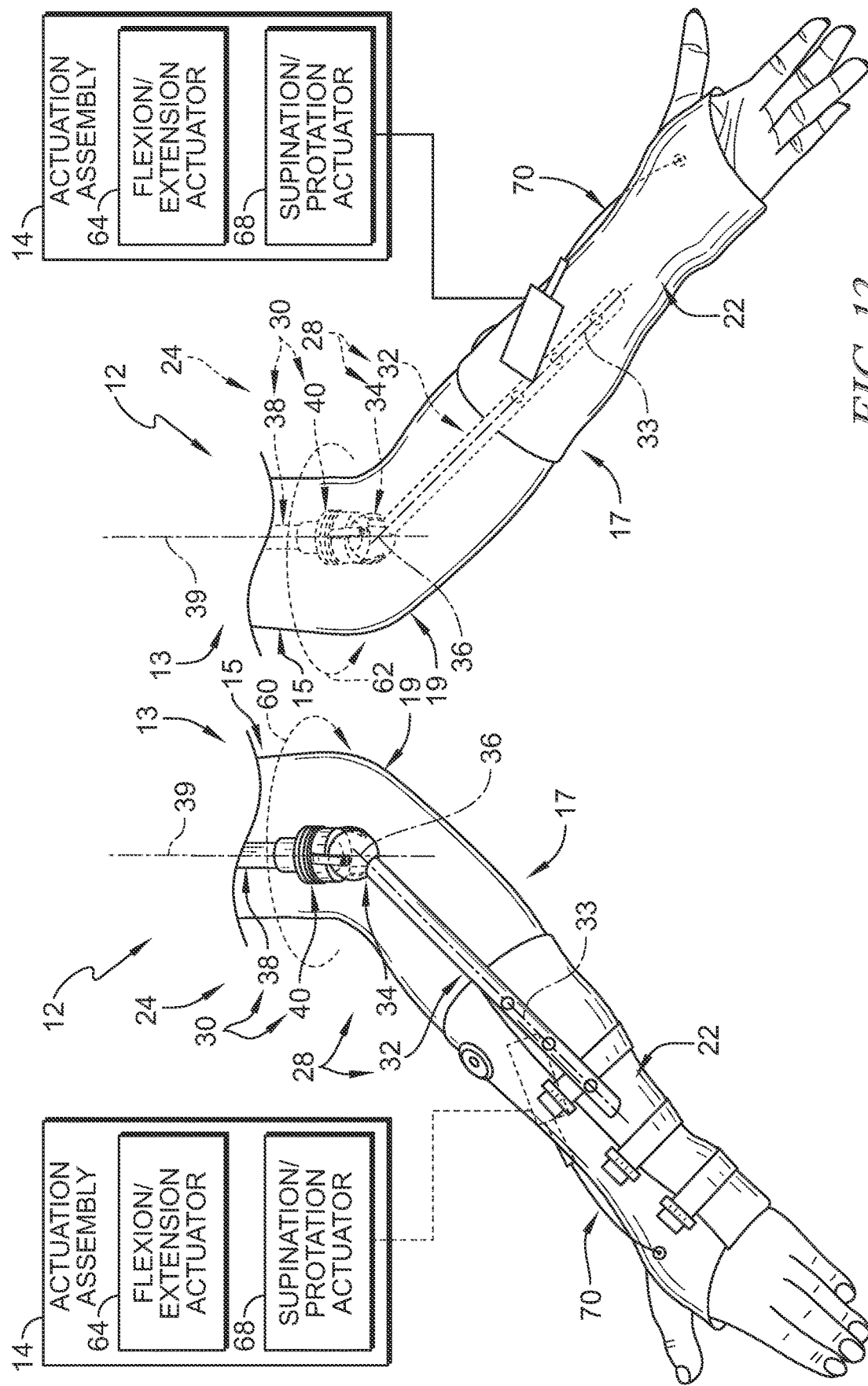
FIG. 11 is a diagrammatic perspective view of the orthopedic device of FIG. 8 showing the actuation assembly in a first linear position to cause the multiaxial joint to be in the pronated arrangement.
FIG. 12 is a view similar to FIG. 11 showing the actuation assembly has been engaged to move to a second linear position to cause the multi-axial joint of the orthopedic brace to move from the pronated arrangement to the supinated arrangement.

The detachable actuation assembly 14 includes a first actuator 64, a first actuator block 66, a second actuator 68, and a wire 70 as shown in FIGS. 13-19. The first actuator 64 is a rotary servo motor 64 and is coupled to the multiaxial joint 24 by the first actuator block 66. The first actuator 64 is configured to change between a first position as shown in FIG. 9 and a second position as shown in FIG. 10 to move the upper portion 20 and the lower portion 22 of the brace 12 in the flexion direction and the extension direction between the flexed and extended arrangements. The second actuator 68 is a linear actuator 68 that is coupled to the lower portion 22 of the brace 12 through the wire 70. The second actuator 68 is configured to change between an extended position as shown in FIGS. 11 and 13 and a retracted position as shown in FIGS. 12 and 14 to move the upper portion 20 and the lower portion 22 of the brace 12 in the supination direction and the pronation direction between the supinated and pronated arrangements.

In the illustrative embodiment, the first actuator block 66 has a concave surface 67 as shown in FIG. 13. The concave surface 67 is shaped to match the outer surface 35 of the ball 34. The first actuator block 66 is configured to minimize the lateral force on the rotor of the first actuator 64.

The first actuator 64 is configured to rotate in a first direction 72 and a second direction 74 opposite the first direction 72 as shown in FIGS. 9 and 10. The first actuator 64 rotates in the first direction 72 from the first position to the second position to move the brace 12 in the flexed direction 56. Conversely, the first actuator 64 rotates in the second direction 74 from the second position to the first position to move the brace 12 in the extended direction 58.

The second actuator 68 is configured to retract in a first linear direction 76 and extend in a second liner direction 78 opposite the first linear direction 76 as shown in FIGS. 13 and 14. The second actuator 68 retracts in the first linear direction 76 from the extended position to the retracted position to move the brace 12 in the supinated direction 62. Conversely, the second actuator 68 extends in the second linear direction 78 from the retracted position to the extended position to allow the brace 12 to move in the pronated direction 60.

The first actuator 64 is configured to move between a plurality of positions between the first and second positions. Similarly, the second actuator 68 is configured to move between a plurality of positions between the extended and retracted positions. The actuators 64, 68 move between the plurality of positions to achieve any one of the plurality of predetermined arrangements of the brace 12.

In the illustrative embodiments, the actuators 64, 68 include rechargeable batteries. The actuators 64, 68 may be detached from the brace 12 to charge the batteries when the brace 12 is not in use. In some embodiments, one actuator 64, 68 may be detached to charge, and another actuator 64, 68 that is fully charged may be attached in place of the charging actuator 64, 68.

The control unit 16 includes a controller 80, a memory 82, and sensors 84 as shown in FIGS. 1 and 8. The controller 80 is a micro-computer 80 that is coupled to the first actuator 54 and the second actuator 68 and is configured to control the actuation of the first actuator 64 and the second actuator 68 by directing the batteries to provide power to the actuator 64, 68. The memory 82 is in communication with the controller 80 and is configured to store user information, predetermined activities, and any data received by the controller 80. The sensors 84 are configured to be arranged on different muscles of the user 11 to measure muscle response or electrical activity in response to nerve stimulation in the muscles.

The controller 80 is configured to direct the first actuator 64, the second actuator 68, or both actuators 64, 68 to move to predetermined positions to cause the brace 12 to move a predetermined arrangement in response to a signal received by the controller 80 from the sensors 84. The predetermined position of the actuator 64, 68 is one of the plurality of positions. The predetermined arrangement included in the plurality of predetermined arrangements of the multi-axial joint 24 is associated with one of or a combination of the positions of the actuators 64, 68.

The signal received by the controller 80 is associated with one of the predetermined arrangement included in the plurality of predetermined arrangements. In other embodiments, the signal received by the controller 80 may be associated with a predetermined activity that is pre-programmed and stored on the memory 82. The predetermined activity includes a plurality of instructions to direct one or both of the actuators 64, 68 to move the multi-axial joint 24 through a series of movements in the different directions 56, 58, 60, 62.

In the illustrative embodiment, the sensors 84 are electromyography (EMG) sensors. The EMG sensors 84 measure muscle response or electrical activity in response to nerve stimulation in the muscles. The signal is a predetermined threshold of electrical activity, or voltage, measured by the EMG sensor 84.

The controller 80 is configured to direct the actuators 64, 68 to move between the different positions once the signal measured by the sensor 84 is above the predetermined threshold. In some embodiments, one sensor 84 may be placed on a muscle of the user 11, while another sensor 84 may be placed on a different muscle of the user 11. If the controller 80 receives a signal from the first sensor 84, the controller 80 directs the actuators 64, 68 to move to the predetermined position. However, if the controller 80 receives a signal from the second sensor 84 on the different muscle of the user 11, the controller 80 may direct the actuators 64, 68 to move to a different predetermined position. The control unit 16 may include more than two sensors 84 in some embodiments.

In other embodiments, the sensor 84 may be a motion detector and the signal may be a detection of motion from the user 11, the doctor/physician, or another person. In some embodiments, the motion detected by the sensor 84 may be facial motion from the user 11.

In some embodiments, the control unit 16 includes a user interface 86 as shown in FIGS. 1 and 8. The user interface 86 is coupled to the controller 80 and configured to receive an input from the user 11 or a physician instructing the user 11 through rehabilitation. The input is a selection of one of the predetermined activities from the memory 82. Upon selection of one of the predetermined activities, the controller 80 receives the signal and is configured to direct one or both of the actuators 64, 68 to move the brace 12 to a predetermined arrangement and/or through a series of motions to different predetermined arrangements.

In some embodiments, the user interface 86 may be a wireless device such as a remote. In some embodiments, the user interface 86 may be an app or program on a phone or tablet. In other embodiments, the user interface 86 may be a button or a knob.

To use the orthopedic device 10, the user 11 may attach the upper portion 20 to the upper arm 15 and attach the lower portion 22 to the forearm 17 so that the multi-axial joint 24 is proximate or centered on the joint 19 of the user's limb 13. With the brace 12 secured to the user 11, the actuation assembly 14 may be selectively attached to the brace 12. In other embodiments, the actuation assembly 14 may be attached to the brace 12 before the user 11 wears the brace 12 on the limb 13.

To attach the actuation assembly 14 to the brace 12, the first and second actuators 64, 68 are coupled to the brace 12. To couple the first actuator 64 to the brace 12, the first actuator block 66 with the first actuator 64 attached is coupled to the ball 34 of the multi-axial joint 24. In other embodiments, the first actuator block 66 is magnetic and coupled to the ball 34 by producing a magnetic force between the block 66 and the ball 34 so as to draw the block 66 and the ball 34 towards one another.

To couple the second actuator 68 to the brace 12, the second actuator 68 is coupled to one of the upper portion 20 and the lower portion 22 of the brace 12. In the illustrative embodiment, the second actuator 68 is coupled to the lower portion 22. The second actuator 68 is coupled to the lower portion 22 at a location proximate to the muscle of the arm 13 that pronates/supinates the arm 13. In other embodiments, the second actuator 68 may be coupled to the brace 12 in another location. The wire 70 is then coupled to the lower portion of the brace 12 and the second actuator 68.

In the illustrative embodiment, both actuators 64, 68 are coupled to the brace 12 simultaneously. In other embodiments, only one actuator 64, 68 may be coupled to the brace 12 at once. In such embodiments, the brace 12 may be locked into a predetermined position by the locking assembly 26 and the actuator 64, 68 moves the brace 12 that predetermined position. Once the actuation assembly 14 is attached to the brace 12, the sensors 84 may be placed in the predetermined locations on the user 11.

Figure 27:
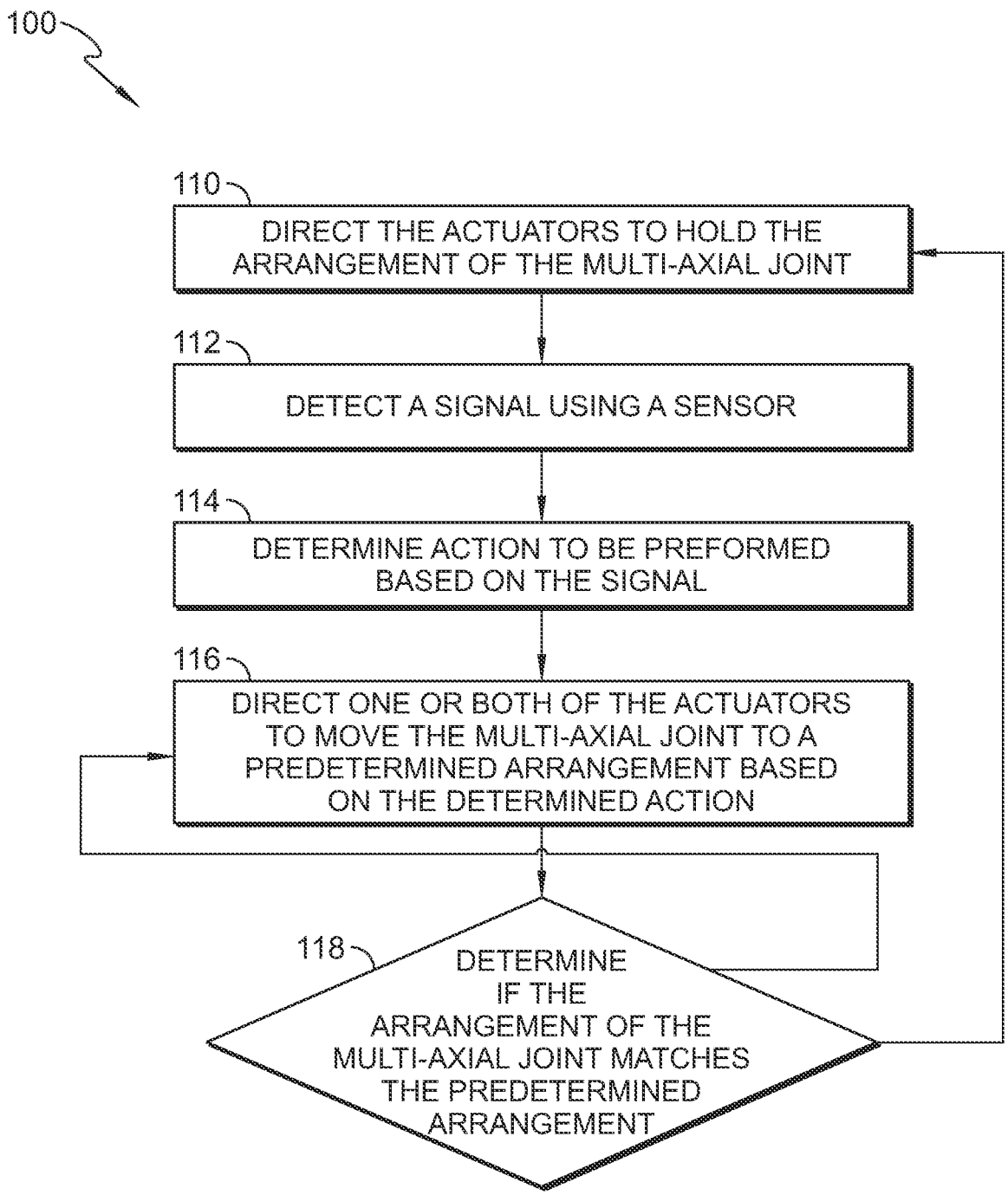
FIG. 27 is a diagrammatic view of a method of controlling the actuation assembly of the orthopedic device based on signals received by sensors included in the control unit.
Figure 28:
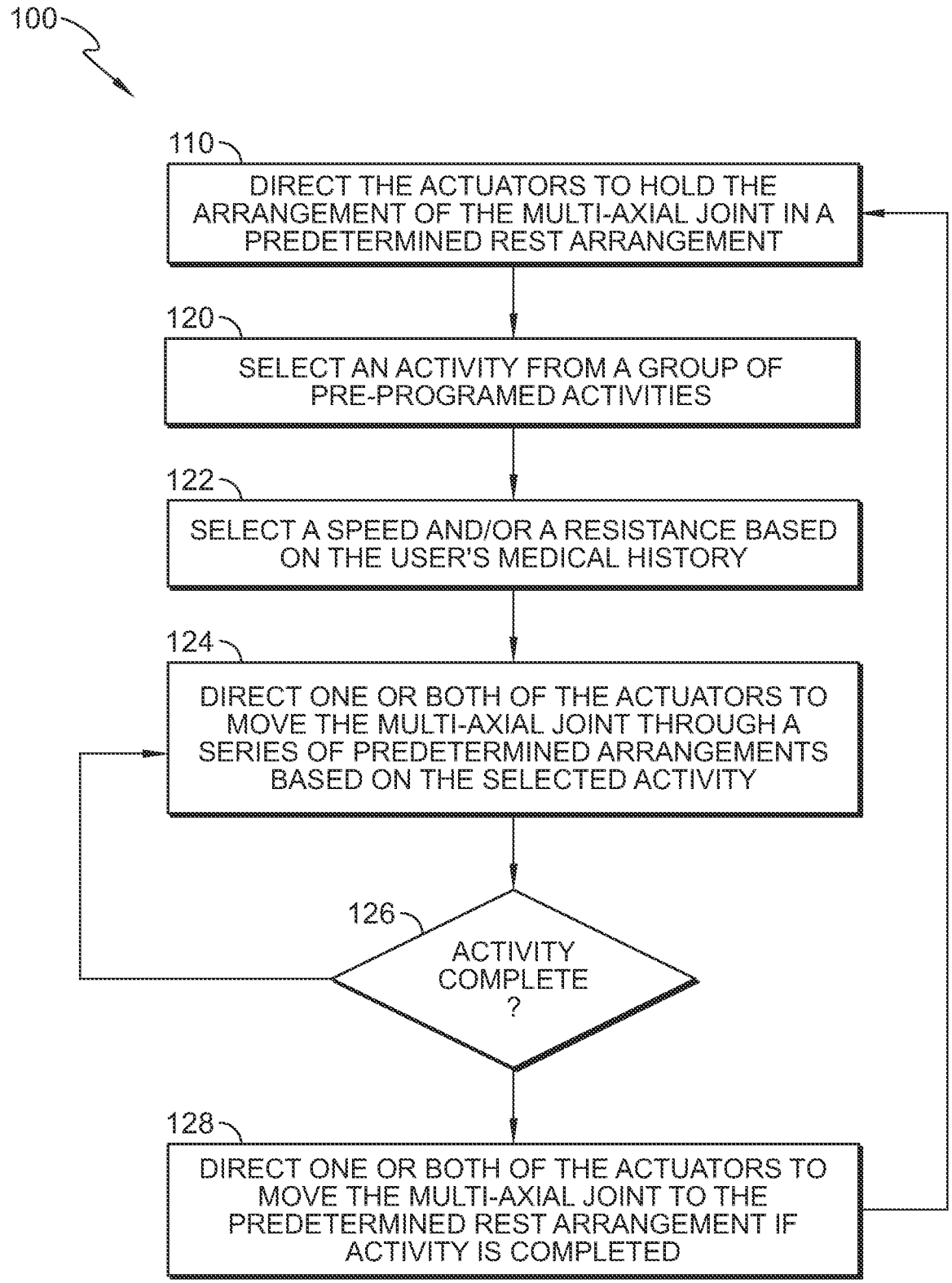
FIG. 28 is a diagrammatic view of another embodiment of a method of controlling the actuation assembly of the orthopedic device in which the device is controlled by selecting different pre-programmed activities stored in the control unit.

A method 100 of controlling the actuation assembly 14 may include several steps as shown in FIGS. 27 and 28. Once the sensors 84 are placed in the predetermined locations on the user 11, the controller 80 may then direct the actuator assembly 14 to move the multi-axial joint 24 to a hold arrangement as indicated by block 110. The hold arrangement may be a resting arrangement for the user 11 or another arrangement selected by the physician or the pre-programmed activity.

Once the sensors 84 detect a signal that is above the predetermined threshold, the controller 80 receives the signal from the sensors 84 as indicated by block 112. The controller 80 then determines the action to be performed based on the signal as indicated by block 114. The action to be performed may include moving the multi-axial joint 24 in a certain direction 56, 58, 60, 62, or to a predetermined arrangement.

The controller 80 then directs one or both actuators 64, 68 to change to move the multi-axial joint 24 to the predetermined arrangement based on the determined action as indicated by block 116. The controller 80 then directs one or both actuators 64, 68 to move the multi-axial joint 24 to the predetermined arrangement by directing the actuators 64, 68 to a predetermined angular or linear position included in the plurality of positions for each actuator 64, 68.

The controller 80 then determines if the arrangement of the multiaxial joint is reached by determining if the actuators 64, 68 have moved to the predetermined position as indicated by block 118. If the controller 80 determines the actuators 64, 68 have reached the predetermined position, then the controller 80 directs the actuators 64, 68 to hold the position so that the brace 12 stays in the resulting arrangement. If the controller 80 determines the actuators 64, 68 have not reached the predetermined position, then the controller 80 directs the actuators 64, 68 to continue to move until the predetermined position is reached.

For example, if the controller 80 receives a signal that is associated with an action of flexing the user's limb 13, the controller 80 directs the actuator 64 to move to the second position to cause the brace 12 to move to the flexed arrangement. The controller 80 then determines if the actuator 64 has reached the second position. If the controller 80 detects the actuator 64 is in the second position, the controller 80 directs the actuator 64 to hold in the second position.

Similarly, if the controller 80 receives a signal that is associated with an action of extending the user's limb 13, the controller 80 directs the actuator 64 to move to the first position to cause the brace 12 to move to the extended arrangement. The controller 80 then determines if the actuator 64 has reached the first position. If the controller 80 detects the actuator 64 is in the first position, the controller 80 directs the actuator 64 to hold in the first position.

Similarly, if the controller 80 receives a signal that is associated with an action of supinating the user's limb 13, the controller 80 directs the actuator 68 to move to the retracted position to cause the brace 12 to move to the supinated arrangement. The controller 80 then determines if the actuator 68 has reached the retracted position. If the controller 80 detects the actuator 68 is in the retracted position, the controller 80 directs the actuator 68 to hold in the retracted position.

Similarly, if the controller 80 receives a signal that is associated with an action of pronating the user's limb 13, the controller 80 directs the actuator 68 to move to the extended position to cause the brace 12 to move to the pronated arrangement. The controller 80 then determines if the actuator 68 has reached the pronated position. If the controller 80 detects the actuator 68 is in the pronated position, the controller 80 directs the actuator 68 to hold in the pronated position.

The controller 80 does not take an initial calibration signal from the sensors 84 to calibrate the signal levels. Rather, the controller 80 is configured to receive a signal from the sensor 84 and determine if the signal received is above a predetermined threshold. If the controller 80 determines the signal is above a predetermined threshold, the controller 80 directs the actuator(s) 64, 68 to move to the predetermined position.

In another embodiment, the method 100 may include controlling actuation of the actuation assembly 14 based on pre-programmed activities as shown in FIG. 28. The controller 80 may direct the actuator assembly 14 to hold the arrangement of the multi-axial joint 24 in a predetermined hold or rest arrangement as indicated by block 110.

The user 11 or physician may then select the pre-programmed activity from a group of pre-programmed activities stored on the memory 82 as indicated by block 120. The user 11 may select the pre-programmed activity using the user interface 86. In some embodiments, the user 11 or physician may select a speed and/or resistance of the actuators 64, 68 based on the user's rehabilitation schedule or prior medical history stored on the memory 82 as suggested by block 122.

Once the controller 80 receives the signal associated with the preprogrammed activity, the controller 80 then directs one or both actuators 64, 68 to move the multi-axial joint 24 through a series of predetermined arrangements based on the predetermined activity as indicated by block 124. In some embodiments, the signal detected by the sensors 84 may be associated with the pre-programmed activity.

For example, if the controller 80 receives a signal that is associated with a pre-programmed activity flexing/extending the user's limb 13, the controller 80 directs the actuator 64 to move to the second position to cause the brace 12 to move to the flexed arrangement. The controller 80 then determines if the actuator 64 has reached the second position. If the controller 80 detects the actuator 64 is in the second position, the controller 80 directs the actuator 64 to hold in the second position for a predetermined amount of time before moving back to the first position.

The controller 80 directs the actuator 64 to move to the first position to cause the brace 12 to move to the extended arrangement. The controller 80 then determines if the actuator 64 has reached the first position. The controller 80 determines once the activity is complete as indicated by block 126.

If the controller 80 determines the activity is complete, the controller 80 directs one or both actuators 64, 68 to move the multi-axial joint 24 to the predetermined rest arrangement as indicated by block 128. Once the multi-axial joint 24 is in the predetermined rest arrangement, the controller 80 directs one of both actuators 64, 68 to hold the multi-axial joint 24 in the predetermined rest arrangement as indicated by block 112. If the activity is not complete, the controller 80 directs one or both actuators 64, 68 to continue with the series of movements until the pre-programmed activity is determined to be complete.

Another embodiment of a detachable actuation assembly 214 in accordance with the present disclosure is shown in FIGS. 15-20. The actuation assembly 214 is substantially similar to the actuation assembly 14 shown in FIGS. 1-14 and described herein. Accordingly, similar reference numbers in the 200 series indicate features that are common between the actuation assembly 14 and the actuation assembly 214. The description of the actuation assembly 14 is incorporated by reference to apply to the actuation assembly 14, except in instances when it conflicts with the specific description and the drawings of the actuation assembly 214.

The detachable actuation assembly 214 includes a first actuator 264, a first actuator block 266, a second actuator 268, and a second actuator block 270 as shown in FIGS. 13-19. The first and second actuators 264, 268 are rotary servo motors 264, 268 and that are coupled to the multi-axial joint 24 by the respective blocks 266, 270.

The first actuator 264 is configured to move the upper and lower portions 20, 22 of the brace 12 in the flexion direction 56 and the extension direction 58 between the flexed and extended arrangements. The second actuator 268 is configured to move the upper and lower portions 20, 22 of the brace 12 in the supination direction 60 and the pronation direction 62 between the supinated and pronated arrangements. The detachable actuator assembly 214 is configured to be actuated by the control unit 16.

In the illustrative embodiment, the first and second actuator blocks 266, 270 have a concave surface 267, 271 as shown in FIGS. 17-20. Each concave surface 267, 271 is shaped to match the outer surface 35 of the ball 34. Each of the actuator blocks 266, 270 are configured to minimize the lateral force on the rotor of the actuators 264, 268.

Figure 18:
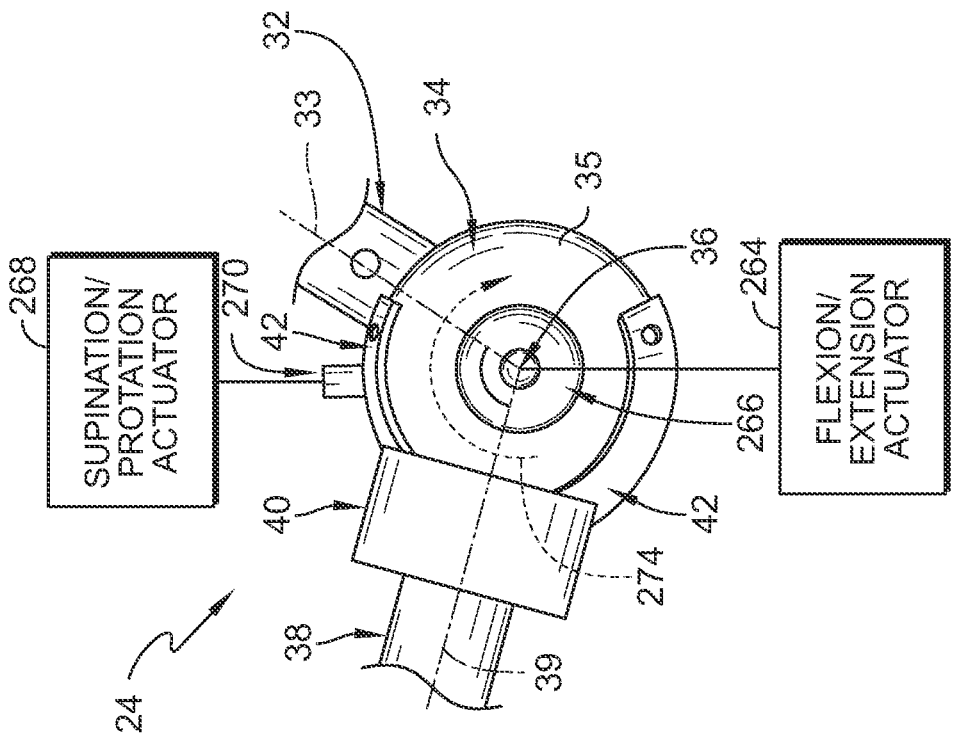
FIG. 18 is a view similar to FIG. 17 in which the actuation assembly has been engaged to move to a second position to cause the multi-axial joint of the orthopedic brace to move from the extended arrangement to the flexed arrangement.
Figure 17:
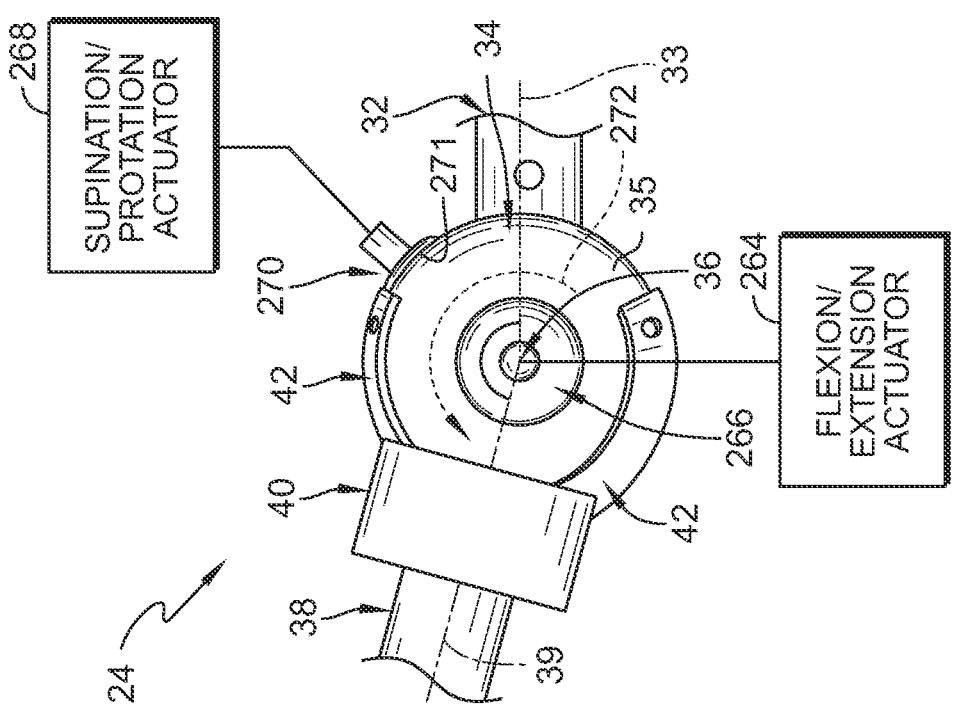
FIG. 17 is a diagrammatic elevation view of the orthopedic device of FIG. 15 showing the actuation assembly in a first position to cause the multi-axial joint of the orthopedic brace to be in the extended arrangement.

The first actuator 264 is configured to rotate in a first direction 272 and a second direction 274 opposite the first direction as shown in FIGS. 17 and 18. The first actuator 264 rotates in the first direction 272 to move the brace 12 in the flexed direction 56. Conversely, the first actuator 264 rotates in the second direction 274 to move the brace 12 in the extended direction 58.

Figure 20:
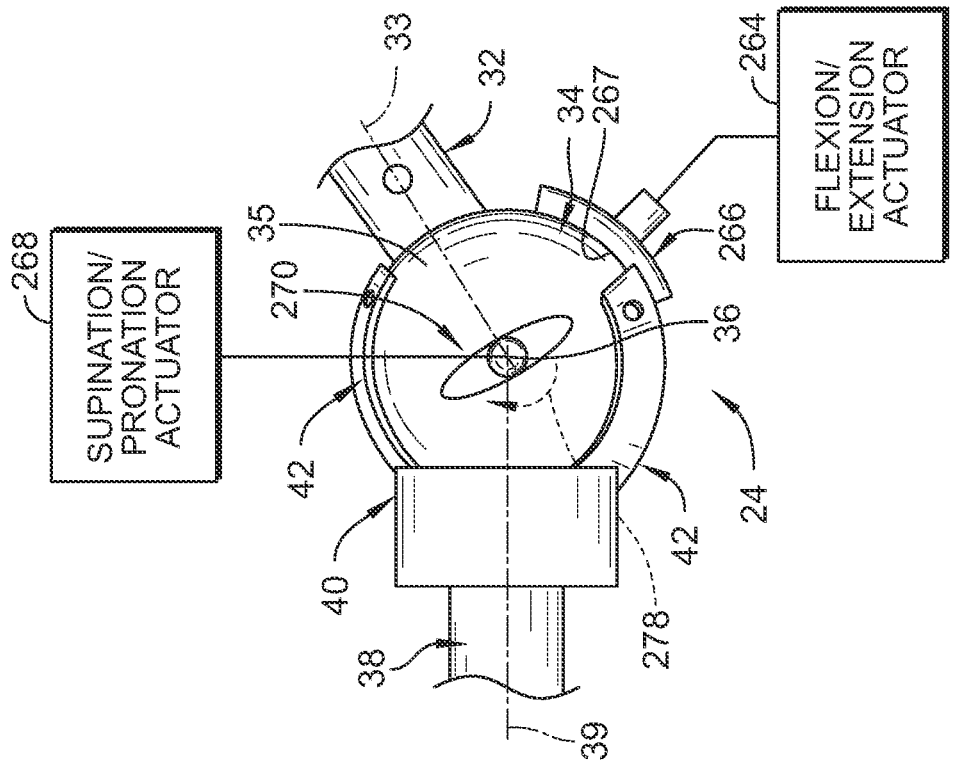
FIG. 20 is a view similar to FIG. 19 in which the actuation assembly has been engaged to move to a fourth position to cause the multi-axial joint of the orthopedic brace to move from the pronated arrangement to the supinated arrangement.
Figure 19:
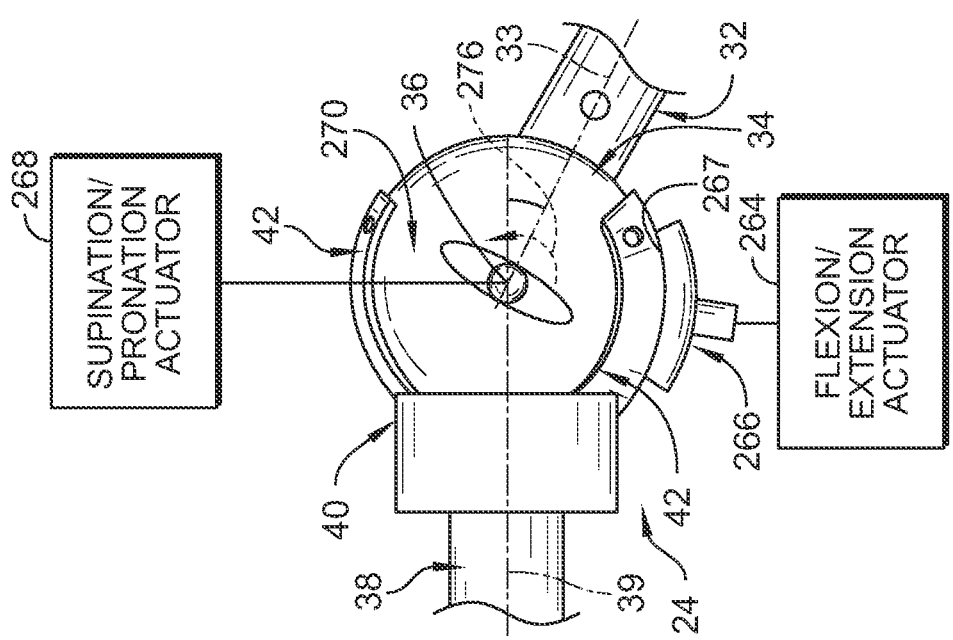
FIG. 19 is a diagrammatic aerial view of the orthopedic device of FIG. 15 showing the actuation assembly in a third position to cause the multiaxial joint of the orthopedic brace in the pronated arrangement.
Figure 21:
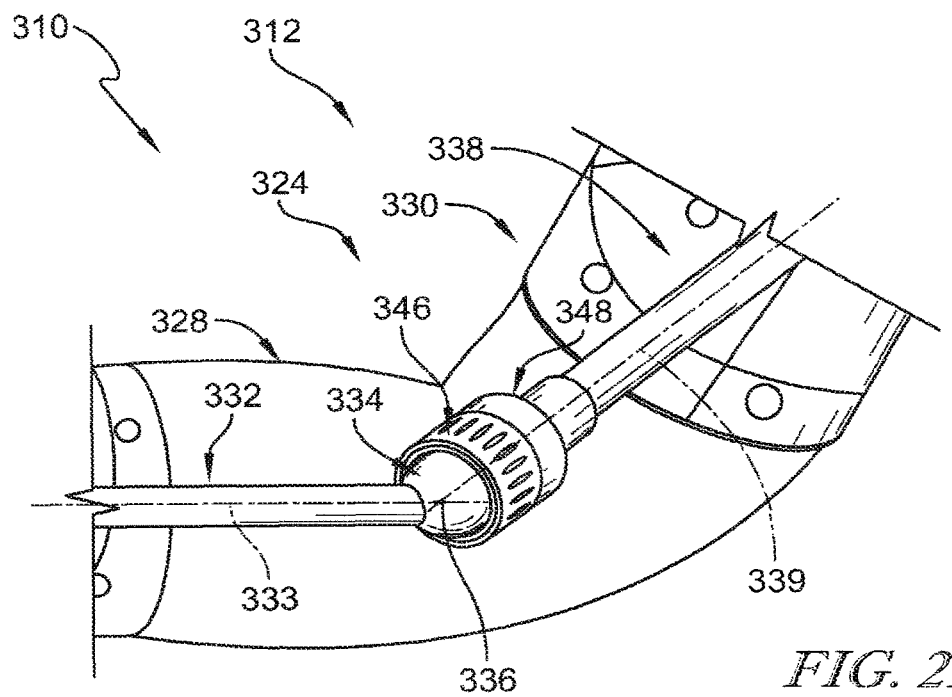
FIG. 21 is another embodiment of the multi-axial joint included in the orthopedic brace of the orthopedic device of FIG. 1 showing the multi-axial joint is a ball and socket joint that includes a rotatable ball portion and socket portion.

The second actuator 268 is configured to rotate in a third direction 276 and a fourth direction 278 opposite the third direction 276 as shown in FIGS. 19 and 20. The second actuator 268 rotates in the third direction 276 to move the brace 12 in the supinated direction 62. Conversely, the second actuator 268 rotates in the fourth direction 278 to move the brace 12 in the pronated direction 64.

Another embodiment of a multi-axial joint 324 in accordance with the present disclosure is shown in FIGS. 21-25. The multi-axial joint 324 is substantially similar to the multi-axial joint 24 shown in FIGS. 1-7 and described herein. Accordingly, similar reference numbers in the 300 series indicate features that are common between the multi-axial joint 24 and the multi-axial joint 324. The description of the multi-axial joint 24 is incorporated by reference to apply to the multi-axial joint 324, except in instances when it conflicts with the specific description and the drawings of the multi-axial joint 324.

The multi-axial joint 324 is a ball and socket joint 324 as shown in FIGS. 21-25. The ball and socket joint 324 includes a rotatable ball portion 328 and a socket portion 330 that forms a ball socket 344 to receive the rotatable ball portion 328.

The rotatable ball portion 328 includes a ball arm 332 that extends along a center ball axis 333 and a ball 334 as shown in FIGS. 21-25. The ball arm 332 is coupled to the lower portion 22 of the orthopedic brace 12. The ball 334 is coupled to one end of the ball arm 332 with a center 336 located on the center axis 333 of the ball arm 332.

The socket portion 330 includes a socket arm 338 that extends along a center socket axis 339 and a socket housing 340 as shown in FIGS. 21-25. The socket arm 338 is coupled to upper portion 20 of the orthopedic brace 12. The socket housing 340 is coupled to one end of the socket arm 338.

The socket housing 340 forms the ball socket 344 as shown in FIGS. 21-25. The ball 334 is located in the ball socket 344 to couple the rotatable ball portion 328 to the socket portion 330 and from the multi-axial joint 324. The ball 334 is free to rotate about the center 336 in the ball socket 344.

Figure 22:
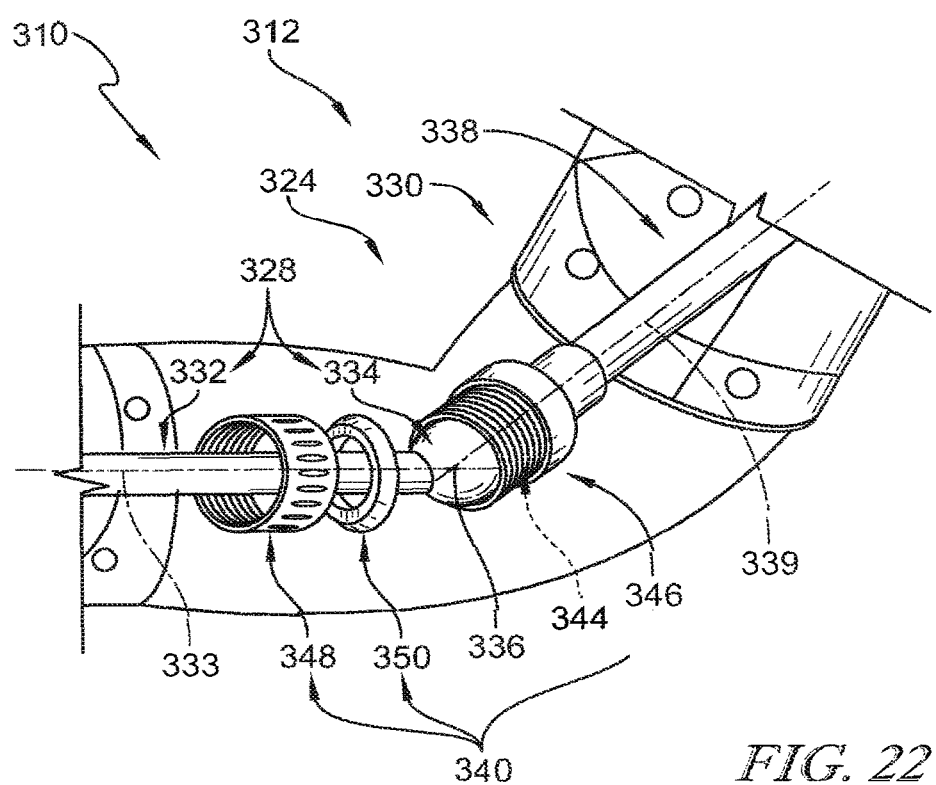
FIG. 22 is an exploded view of the multi-axial joint of FIG. 21 showing the socket portion includes a main portion and a cover configured to be screwed onto the main portion of the socket portion over the ball portion to hold the ball portion in the socket portion.

In the illustrative embodiments, the socket housing 340 includes a main portion 346, a cover 348, and a seal 350 as shown in FIG. 22. The main portion 346 and the cover 348 together define the ball socket 344. The cover 348 is configured to be screwed onto the main portion 346 over the ball 334.

The cover 348 is configured to lock the ball 334 from rotating in the ball socket 344. The cover 348 acts as a locking assembly 26 to block rotation of the ball 334 in the ball socket 344 of the housing 340. The cover 348 may be screwed on and further tightened to engaged the ball 334 and lock the ball 334 from rotating.

Figure 23:
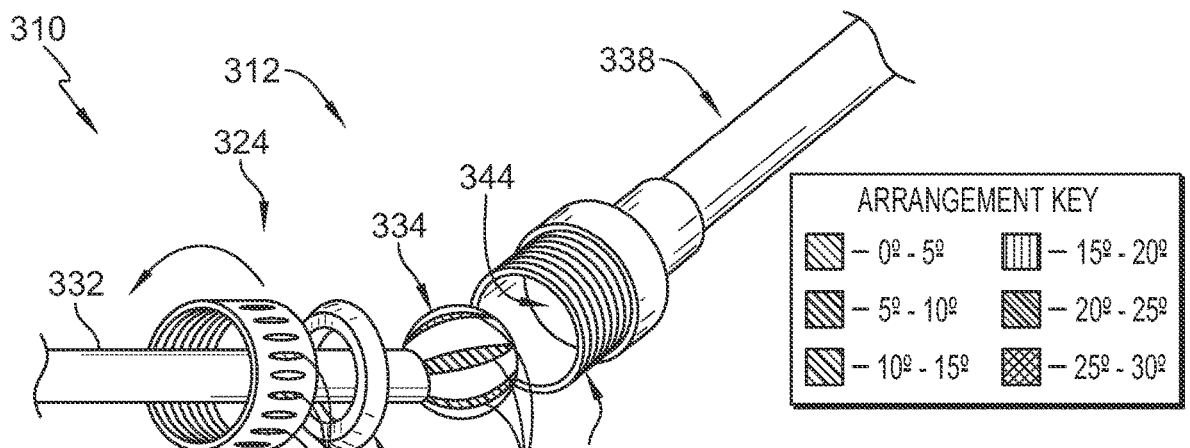
FIG. 23 is a view similar to FIG. 22 showing the multi-axial joint includes a plurality of position indicators that aid in locking the multi-axial joint in different predetermined arrangements.
Figure 24:
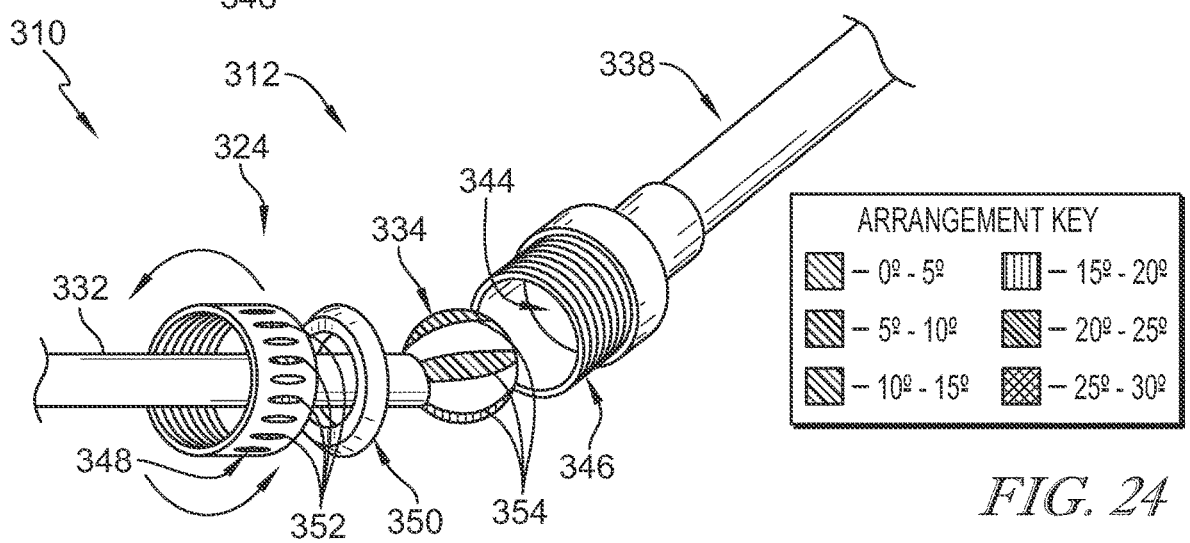
FIG. 24 is a view similar to FIG. 21 showing the plurality of position indicators formed on the cover of the joint aligned with position indicators formed on the main portion in a different predetermined arrangement.
Figure 25:
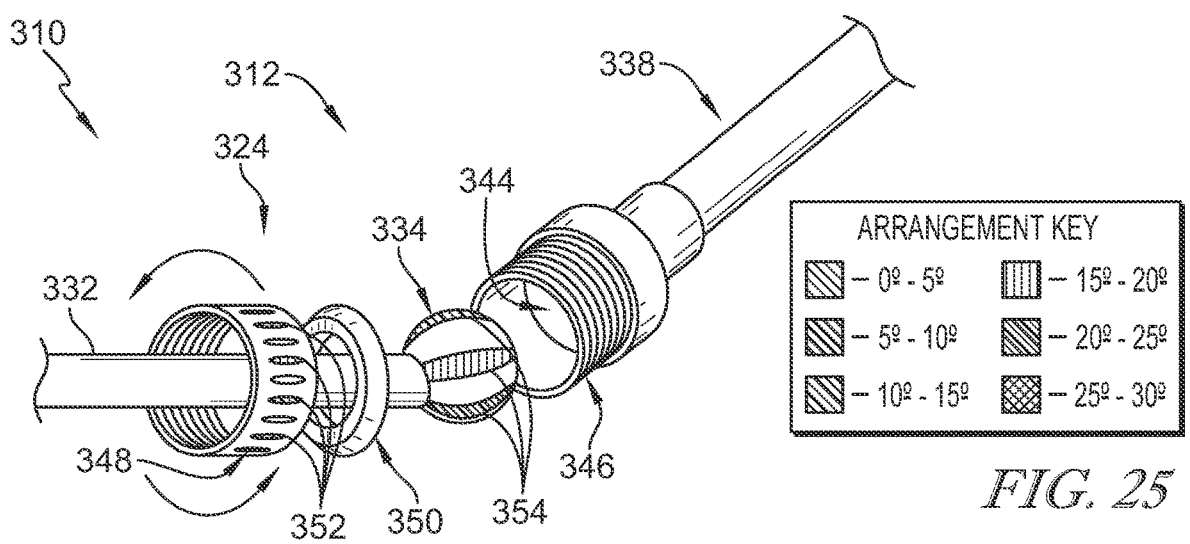
FIG. 25 is a view similar to FIG. 24 showing the plurality of position indicators formed on the cover of the joint aligned with position indicators formed on the main portion in a different predetermined arrangement.

The cover 348 may further include a plurality of position indicators 352 as shown in FIGS. 23-25. The plurality of position indicators 352 are configured to be aligned with the corresponding indicators 354 on the ball 334 to lock the joint 324 in different predetermined arrangements. The indicators 352, 354 are formed in the joint 324 so that when they are aligned in different combinations the result is a predetermined arrangement associated with a predetermined angle as shown in FIGS. 23-25. The indicators help the user 11 or physician lock the joint 24 in the desired predetermined position for a certain exercise or arrangement of the brace 12.

Figure 26:
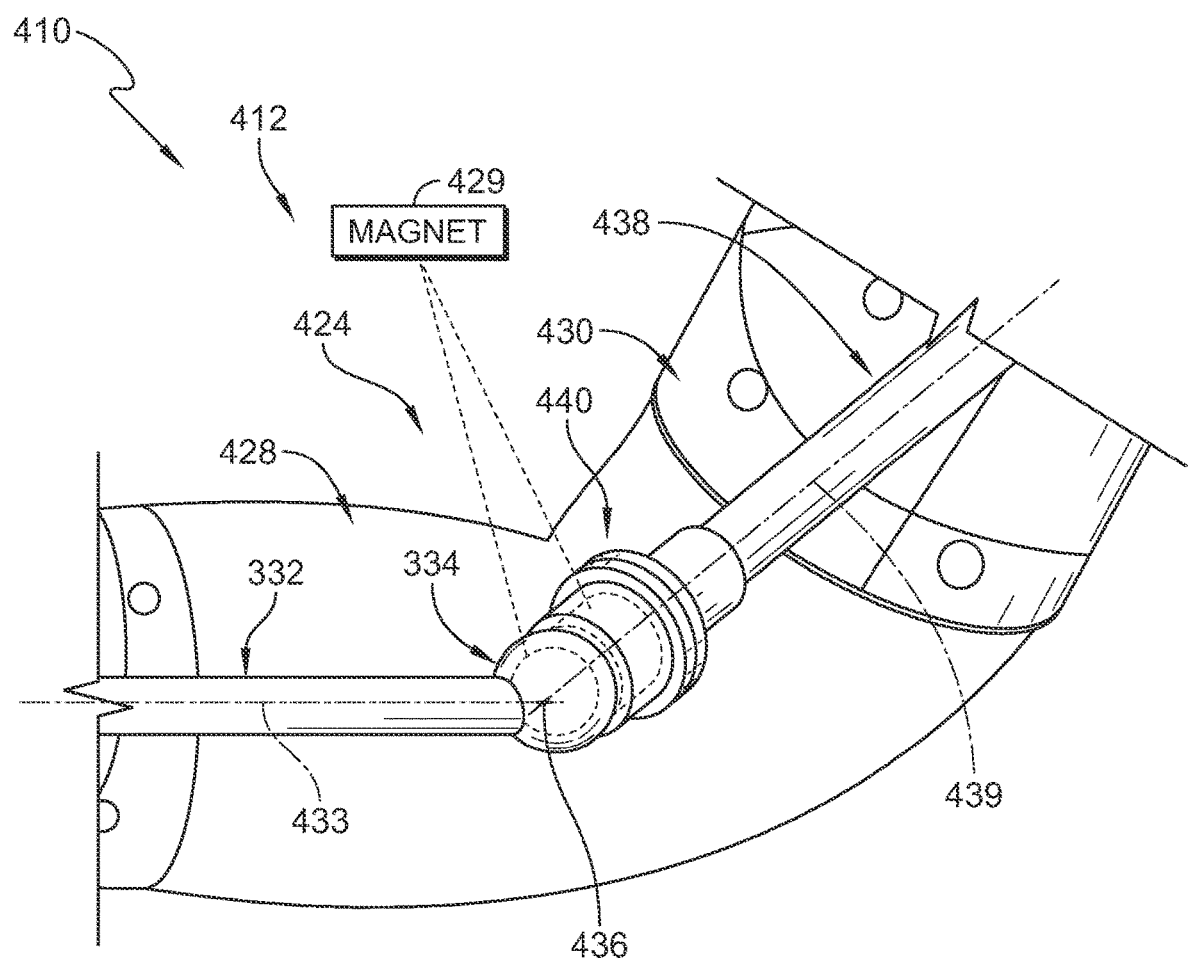
FIG. 26 is another embodiment of the multi-axial joint included in the orthopedic brace of the orthopedic device of FIG. 1 showing the multi-axial joint is a ball and socket joint that has a magnetic ball portion that couples to a socket housing of the ball and socket joint.

Another embodiment of a multi-axial joint 424 in accordance with the present disclosure is shown in FIG. 26. The multi-axial joint 424 is substantially similar to the multi-axial joint 24 shown in FIGS. 1-14 and described herein. Accordingly, similar reference numbers in the 400 series indicate features that are common between the multi-axial joint 24 and the multi-axial joint 424. The description of the multi-axial joint 24 is incorporated by reference to apply to the multi-axial joint 424, except in instances when it conflicts with the specific description and the drawings of the multi-axial joint 424.

The multi-axial joint 424 is a ball and socket joint 424 as shown in FIG. 26. The ball and socket joint 424 includes a rotatable ball portion 428 and a socket portion 430 that forms a ball socket 444 to receive the rotatable ball portion 428.

In the illustrative embodiment, the rotatable ball portion 428 includes a magnet 429 as suggested in FIG. 26. The magnet 429 produces a magnetic force between the ball portion 428 and the socket portion 430 so as to draw the ball portion 428 and socket portion 430 towards one another.

The rotatable ball portion 428 includes a ball arm 432 that extends along a center ball axis 433 and a ball 434 as shown in FIG. 26. The ball arm 432 is coupled to the lower portion 22 of the orthopedic brace 12. The ball 434 is coupled to one end of the ball arm 432 with a center 436 located on the center axis 433 of the ball arm 432.

The socket portion 430 includes a socket arm 438 that extends along a center socket axis 439 and a socket housing 440 as shown in FIG. 26. The socket arm 438 is coupled to upper portion 20 of the orthopedic brace 12. The socket housing 440 is coupled to one end of the socket arm 438.

In the illustrative embodiment, the ball 434 houses the magnet 429. The different actuators (not shown) may be coupled to the ball 434 using the magnet 429 to produce a magnetic force between the ball 434 and the actuator so as to hold the actuator to the ball 434. In other embodiments, the socket housing 440 includes the magnet 429 as suggested in FIG. 26.

The present disclosure relates to a low profile, multifunctional orthopedic device 10, 210, 310, 410 with a lightweight exoskeletal 12, 312, 412 to improve and aid in anatomically correct range or motion and rehabilitation. The orthopedic device 10, 210, 310, 410 may be adaptable to also aid in personal independence via muscular contraction that registers to a microcomputer 80. The microcomputer or controller 80 then activates the brace 12, 214, 314, 414 to passively flex and extend an arm 13 of the patient or user 11. In this way, the patient 11 gains some personal independence all without surgery or implanted devices.

The orthopedic device 10, 210, 310, 410 is an affordable product ideal for patient's that have suffered hemiplegia or paraplegia from stroke or other type of injury or illness. Amyotrophic lateral sclerosis (ALS) patients may be another ideal patient that would greatly benefit from using the brace 12, 214, 314, 414. As the patient 11 gradually lose function of their extremity, the orthopedic device 10, 210, 310, 410 may aid in extending their feeling of independence.

The orthopedic device 10, 210, 310, 410 allows any patient 11 that can contract any muscle in their body to use the brace 12, 214, 314, 414. The sensors 84 are configured to pick up or detect action potentials from any muscle. Once the potential reaches a certain threshold, a signal is given to the controller 80 and the actuators 64, 68, 264, 268 are directed to the predetermined position. This will not only will give the patient 11 independence, but allow the care giver peace of mind that the patient 11 can take a sip of water or scratch their nose, even if they are not directly by their side.

In addition to physical independence, the orthopedic device 10, 210, 310, 410 may be adapted for protection of the elbow 19 post injury, protection of the elbow 19 post-surgery, assistance in rehabilitation of the elbow 19, and prevention of elbow 19 contracture post trauma/medical illness. The orthopedic device 10, 210, 310, 410 may also allow for passive motion on patients 11 with spinal cord injuries, stroke, and/or Parkinson's to prevent contractures of the elbow 19 by being placed on admission to the hospital. As such, the orthopedic device 10, 210, 310, 410 may decrease the need for occupational therapy and may continue through the patient's rehabilitation.

Presently, common orthopedic braces are adapted for passive range of motion and may be costly, home bound, and not utilized due to the lack of use by surgeons. The present orthopedic device 10, 210, 310, 410 may be programmed with feedback that is recorded and stored on the memory 82. The recorded feedback to the device may include a person's range of motion of the elbow 19 and/or patient compliance.

The device 10, 210, 310, 410 may also determine how the joint 19 of the patient 11 is functioning by level of torque feedback to the control unit 16. The level of torque feedback may indicate the stiffness of the joint 19.

The orthopedic device 10, 210, 310, 410 may also decrease the number of occupational therapy visits since the device 10, 210, 310, 410 may be programmed with different rehabilitation activities/exercises. This may allow the patient 11 to complete the activities throughout the day at the patient's convenience.

The flexibility of when and where the patient 11 may do therapy may save the patient 11 on therapy visit payments. Additionally, the device 10, 210, 310, 410 may allow for more new patient slots at the office, which may be limited due to capacity limits and social distancing requirements.

In the illustrative embodiments, the orthopedic device 10, 210, 310, 410 includes EMG sensors 84 to detect signals from the patient 11 to control activation of the actuators 64, 66, 264, 266 to move the multi-axial joint 24. The EMG sensors 84 may allow the patient 11 to move the brace 12 by utilizing activation of their own muscles.

In some embodiments, the orthopedic device 10, 210, 310, 410 may further include a potentiometer. The potentiometer may be incorporated through a user interface 86 to allow the patient to move the brace 12 by turning a dial or knob 86.

The orthopedic device 10, 210, 310, 410 may also include different attachments for different tasks such as drinking, eating, itching, etc. The orthopedic device 10, 210, 310, 410 may include a grabber to attach a cup for drinking or hold utensils for eating. There may be another attachment such as a nose itching device to aid the patient or user in itching their nose.

It should be appreciated that the orthopedic system has a number of advantages, for example it is relatively simple, light weight, is relatively inexpensive, versatile, can easily be put on and taken off, and has a low profile which allows it to be worn under clothing. The orthopedic system is also easy to operate and a patient can be taught how to use it in a short amount of time, e.g. 10 minutes.

While the disclosure has been illustrated and described in detail in the foregoing drawings and description, the same is to be considered as exemplary and not restrictive in character, it being understood that only illustrative embodiments thereof have been shown and described and that all changes and modifications that come within the spirit of the disclosure are desired to be protected.

What is claimed is:

1. An orthopedic device comprising
an orthopedic brace configured to be worn by a user, the orthopedic brace including an upper portion, a lower portion, and a multi-axial mechanical joint extending between and interconnecting the upper portion and the lower portion of the brace, the upper portion of the brace configured to be selectively attached to an upper portion of a limb of the user and the lower portion configured to be selectively attached to a lower portion of the limb of the user such that the multi-axial joint is proximate to a joint of the user between the upper and lower portions, and the multi-axial joint configured to rotate between a plurality of predetermined arrangements,
an assembly coupled to the multi-axial joint of the brace and configured to move the upper and lower portions of the brace between the plurality of predetermined arrangements, the assembly including a first actuator coupled to the multi-axial joint and configured to move the upper and lower portions of the brace in a flexion direction and an extension direction between the plurality of predetermined arrangements, and
a control unit coupled to the assembly and configured to selectively actuate the assembly to move the orthopedic brace to a predetermined arrangement included in the plurality of predetermined arrangements in response to a signal associated with the predetermined arrangement,
wherein the multi-axial joint is a ball and socket joint, the ball and socket joint including a rotatable ball portion including a ball arm extending along a center ball axis and coupled to the lower portion of the orthopedic brace and a ball coupled to one end of the ball arm with a center located on the center axis, and a socket portion including a socket arm that extends along a center socket axis and coupled to the upper portion of the orthopedic brace and a socket housing coupled to one end of the socket arm that forms a ball socket, the socket housing including at least two prongs, wherein the ball is located in the at least two prongs of the ball socket to couple the rotatable ball portion to the socket portion.

2. The orthopedic device of claim 1, wherein the control unit includes
a controller coupled to the first actuator and configured to selectively direct the first actuator to move the orthopedic brace between a first position and a second direction to cause the multi-axial joint to move between the plurality of predetermined arrangements, and
a memory in communication with the controller and configured to receive and store information received by the controller.

3. The orthopedic device of claim 2, wherein the control unit further includes sensors coupled to the user and coupled to the controller to measure electrical activity in response to nerve stimulation in muscles of the user.

4. The orthopedic device of claim 3, wherein the first actuator is a rotary servo motor and configured to change between a first position and a second position to move the upper and lower portions of the brace in the flexion direction and the extension direction between a flexed arrangement and an extended arrangement.

5. The orthopedic device of claim 1, wherein the ball of the ball and socket joint is a magnet.

6. The orthopedic device of claim 1, wherein the ball and socket joint further includes a locking assembly configured to engage the ball of the ball and socket joint to block rotation of the ball in the ball socket of the housing.

7. The orthopedic device of claim 1, wherein the multi-axial joint has a maximum angle between 130 and 140 degrees relative to the center ball axis and the center socket axis between an extended arrangement and a flexed arrangement.

8. The orthopedic device of claim 1, wherein the multi-axial joint has a maximum angle between 100 and 120 degrees relative to the center ball axis and the center socket axis between a pronated arrangement and a supinated arrangement.

9. The orthopedic device of claim 1, wherein the assembly includes a second actuator coupled to the multi-axial joint and configured to move the upper and lower portions of the brace in a supination direction and a pronation direction between the plurality of predetermined arrangements.

10. The orthopedic device of claim 1, wherein the assembly is magnetically coupled to the multi-axial joint of the brace.

11. An orthopedic brace configured to be worn by a user, the orthopedic brace comprising:
an upper portion configured to be selectively attached to an upper portion of a limb of the user, a lower portion configured to be selectively attached to a lower portion of the limb of the user, and a multi-axial joint extending between and interconnecting the upper portion and the lower portion of the brace and proximate to a joint of the user between the upper and lower portions, the multi-axial joint configured to rotate between a flexed arrangement, an extended arrangement, a supinated arrangement, and a pronated arrangement,
wherein the multi-axial joint is a ball and socket joint, the ball and socket joint including a rotatable ball portion including a ball arm extending along a center ball axis and coupled to the lower portion of the orthopedic brace and a ball coupled to one end of the ball arm with a center located on the center axis, and a socket portion including a socket arm that extends along a center socket axis and coupled to the upper portion of the orthopedic brace and a socket housing including at least two prongs coupled to one end of the socket arm that forms a ball socket, wherein the ball is located in the ball socket to couple the rotatable ball portion to the socket portion.

12. The orthopedic brace of claim 11, wherein the ball of the ball and socket joint is a magnet.

13. The orthopedic brace of claim 11, wherein the ball and socket joint further includes a locking assembly configured to engage the ball of the ball and socket joint to block rotation of the ball in the ball socket of the housing.

14. An orthopedic system, comprising:
a brace configured to be placed around an inoperable limb of a patient, the limb having an anatomical joint and at least one inoperable muscle, wherein the brace includes a first component and a second component attached by a mechanical joint, the mechanical joint including a ball and socket joint, the ball and socket joint including a rotatable ball portion including a ball arm, the rotatable ball portion coupled to the first component of the orthopedic brace and a ball coupled to one end of the ball arm, and a socket portion including a socket arm coupled to the second component of the orthopedic brace and a socket housing including at least two prongs coupled to one end of the socket arm that forms a ball socket, wherein the ball is located in the ball socket to couple the rotatable ball portion to the socket portion,
an actuation assembly operably coupled to the first and second components of the brace so that activation of the actuation assembly causes movement of at least one of the components around the joint,
a control unit interfaced with the actuation assembly so the control unit can send an instruction signal to the actuation assembly, and
a sensor configured to be in communication with (i) the control unit and (ii) at least one of the patient's operable muscles, wherein the sensor has a predetermined threshold of detecting contraction of the at least one operable muscle.

15. The orthopedic system of claim 14, wherein the sensor is configured to be spaced apart from the at least one inoperable muscle and placed in communication with an operable muscle that is not operably coupled to the patient's anatomical joint.

16. The orthopedic system of claim 14 wherein, the ball and socket joint extends between and interconnects the first component and the second component of the brace.

17. The orthopedic system of claim 16 wherein, the ball and socket joint is configured to rotate between a plurality of predetermined arrangements.

18. The orthopedic system of claim 14, wherein, the actuation assembly is configured to move the first component and second component of the brace between a plurality of predetermined arrangements.

19. The orthopedic system of claim 16, wherein, the actuation assembly includes a first actuator coupled to the ball and socket joint and a second actuator coupled to the multi-axial joint.

20. A method of operating an orthopedic system having
(i) a brace that includes a first component and a second component attached by a joint, the joint including a ball and socket joint, the ball and socket joint including a rotatable ball portion including a ball arm, the rotatable ball portion coupled to the first component of the orthopedic brace and a ball coupled to one end of the ball arm, and a socket portion including a socket arm coupled to the second component of the orthopedic brace and a socket housing including at least two prongs coupled to one end of the socket arm that forms a ball socket, wherein the ball is located in the ball socket to couple the rotatable ball portion to the socket portion,
(ii) an actuation assembly operably coupled to the first and second components so that activation of the actuation assembly causes movement of at least one of the components around the joint,
(iii) a control unit interfaced with the actuation assembly so the control unit can send a signal to the actuation assembly,
(iv) a sensor operatively coupled to the control unit, the sensor capable of sensing a signal from a voluntary muscle contraction and sending a signal to the control unit to activate the actuation assembly, the method comprises steps of: positioning the brace in contact with a limb of a patient wherein the limb has
   {i} a first bone component and a second bone component attached by a joint and
   {ii} at least one muscle operably coupled to the first bone component and/or second bone component but is incapable of generating a signal; and positioning the sensor on the skin of the patient so the sensor can communicate with a muscle capable of generating a signal, wherein the muscle is not operatively coupled to the first or second bone component.

21. An orthopedic system comprising:
{i} a brace that includes a first component and a second component attached by a joint, the joint including a ball and socket joint, the ball and socket joint including a rotatable ball portion including a ball arm, the rotatable ball portion coupled to the first component of the orthopedic brace and a ball coupled to one end of the ball arm, and a socket portion including a socket arm coupled to the second component of the orthopedic brace and a socket housing including at least two prongs coupled to one end of the socket arm that forms a ball socket, wherein the ball is located in the ball socket to couple the rotatable ball portion to the socket portion,
{ii} an actuation assembly operably coupled to the first and second components so that activation of the actuation assembly causes movement of at least one of the components around the joint,
{iii} a control unit interfaced with the actuation assembly so the control unit can send a signal to the actuation assembly, and
{iv} an extracorporeal device capable of sending a signal to the control unit to actuate the actuation assembly.

22. The orthopedic system of claim 21, wherein, the extracorporeal device is a computer.

23. The orthopedic system of claim 21, wherein, the extracorporeal device is capable of sending an analog or digitized signal to the control unit.

24. The orthopedic system of claim 21, wherein, extracorporeal device is configured so that the signal is initiated by a bite stick operated by a patient.

25. A method of operating an orthopedic system having
{i} a brace that includes a first component and a second component attached by a joint, the joint including a ball and socket joint, the ball and socket joint including a rotatable ball portion including a ball arm, the rotatable ball portion coupled to the first component of the orthopedic brace and a ball coupled to one end of the ball arm, and a socket portion including a socket arm coupled to the second component of the orthopedic brace and a socket housing including at least two prongs coupled to one end of the socket arm that forms a ball socket, wherein the ball is located in the ball socket to couple the rotatable ball portion to the socket portion,
{ii} an actuation assembly operably coupled to the first and second components so that activation of the actuation assembly causes movement of at least one of the components around the joint,
{iii} a control unit interfaced with the actuation assembly so the control unit can send a signal to the actuation assembly,
{iv} a sensor operatively coupled to the control unit, the sensor capable of sensing movement of a body part of a patient and sending a signal to the control unit to actuate the actuation assembly, the method comprising the steps of: positioning the brace in contact with a limb of the patient wherein the limb has
   (i) a first bone component and a second bone component attached by a joint and
   (ii) at least one muscle operably coupled to the first bone component and/or second bone component but incapable of contracting; and positioning the sensor relative to a body part so the sensor can sense movement of the body part and send a signal to the control unit to actuate the actuation assembly.

26. The method of claim 25, wherein the sensor is an electromyography (EMG) sensor.

27. The method of claim 25, wherein the sensor is a mechanomyogram (MMG) sensor.

* * * * *